(12) United States Patent
Feilders et al.

(10) Patent No.: US 8,963,060 B2
(45) Date of Patent: Feb. 24, 2015

(54) AUTOMATED MICROWAVE SAMPLE DIGESTION SYSTEM

(75) Inventors: George Feilders, Beaconsfield (CA); Arthur Ross, Selkirk (CA); Raymond Guay, Dollard-des-Ormeaux (CA)

(73) Assignee: SCP Science, Baie d'Urfe, Quebec (CA)

( * ) Notice: Subject to any disclaimer, the term of this patent is extended or adjusted under 35 U.S.C. 154(b) by 757 days.

(21) Appl. No.: 13/025,465

(22) Filed: Feb. 11, 2011

(65) Prior Publication Data

US 2011/0198345 A1 Aug. 18, 2011

Related U.S. Application Data

(60) Provisional application No. 61/304,387, filed on Feb. 12, 2010.

(51) Int. Cl.
 *H05B 6/78* (2006.01)
 *B01L 9/00* (2006.01)
 *B01J 19/12* (2006.01)
 (Continued)

(52) U.S. Cl.
 CPC ............... *B01L 9/00* (2013.01); *B01J 19/126* (2013.01); *B01L 7/00* (2013.01); *G01N 1/4044* (2013.01); *B01J 2219/1215* (2013.01); *B01J 2219/1218* (2013.01); *B01J 2219/1209* (2013.01);
 (Continued)

(58) Field of Classification Search
 CPC .......... B01L 7/00; B01L 9/00; B01L 3/5082; B01L 9/06; B01L 2300/1866; G01N 1/4044; G01N 1/44
 USPC ................. 219/700–702, 699, 739, 388, 214; 426/242, 234, 466; 34/259, 263–264, 34/266, 92; 432/128, 152; 99/468, 472; 266/92
 See application file for complete search history.

(56) References Cited

U.S. PATENT DOCUMENTS 4,347,216 A 8/1982 Kawasaki et al.
4,834,649 A * 5/1989 Levit et al. .................... 432/121
(Continued)

FOREIGN PATENT DOCUMENTS

EP 549495 6/1993
GB 1135239 12/1968
(Continued)

OTHER PUBLICATIONS

International Search Report dated May 10, 2011 issued by the International Bureau (WIPO) in connection with the corresponding International patent application No. PCT/CA2011/000170.

*Primary Examiner* — Quang Van
(74) *Attorney, Agent, or Firm* — Norton Rose Fulbright Canada LLP

(57) ABSTRACT

There is described an automated heating system for heating a sample contained in a sample holder, comprising: a heating chamber having at least one opening and adapted to receive the sample holder; a microwave generator in microwave transfer communication with the heating chamber; a conveyor extending into the heating chamber and adapted to receive and transport the sample holder into and out of the heating chamber; at least one microwave barrier movable between an open position to allow access to the heating chamber and a closed position to prevent microwaves from leaking out of the heating chamber when the microwave generator is activated; and a control unit for controlling the microwave generator and the conveyor.

22 Claims, 41 Drawing Sheets

(51) Int. Cl.
B01L 7/00 (2006.01)
G01N 1/40 (2006.01)
*B01L 3/00* (2006.01)
*B01L 9/06* (2006.01)
*G01N 1/44* (2006.01)

(52) U.S. Cl.
CPC *B01L3/5082* (2013.01); *B01L 9/06* (2013.01); *B01L 2300/1866* (2013.01); *G01N 1/44* (2013.01)
USPC .......................................... 219/702; 219/700

(56) References Cited

U.S. PATENT DOCUMENTS

| | | | |
|---|---|---|---|
| 5,796,080 A | 8/1998 | Jennings et al. | |
| 5,897,807 A * | 4/1999 | Edgar et al. | 219/700 |
| 5,942,142 A * | 8/1999 | Forney et al. | 219/388 |
| 5,988,877 A | 11/1999 | Hochrad et al. | |
| 6,607,920 B2 | 8/2003 | Jennings et al. | |
| 6,713,741 B2 * | 3/2004 | Miller | 219/700 |
| 7,392,718 B2 | 7/2008 | Emoto | |
| 2004/0238326 A1 * | 12/2004 | Lichti | 198/475.1 |
| 2007/0205859 A1 * | 9/2007 | Webster | 340/5.7 |
| 2008/0064085 A1 | 3/2008 | McArdle | |

FOREIGN PATENT DOCUMENTS

| WO | WO0036880 | 6/2000 |
|---|---|---|
| WO | WO2009036186 | 3/2009 |

* cited by examiner

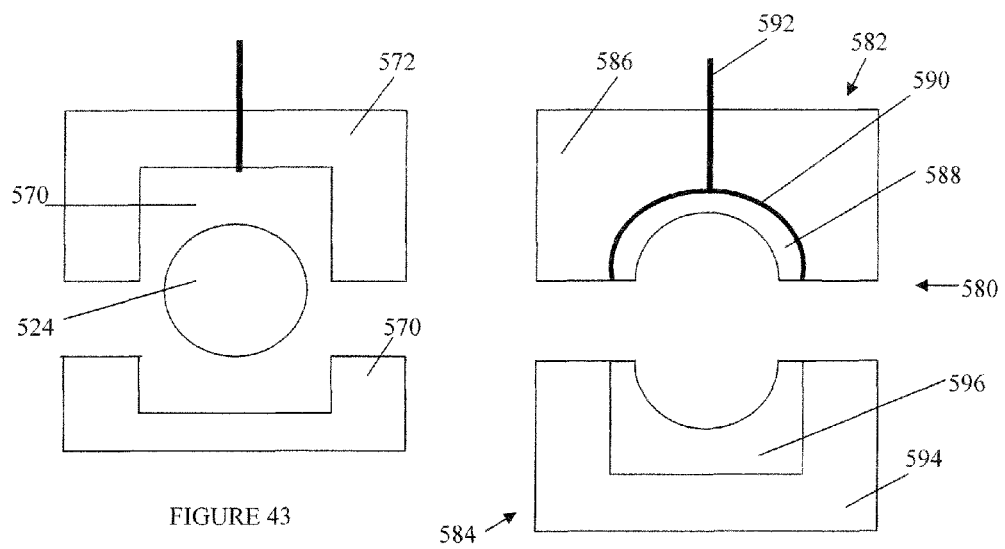
FIGURE 43
FIGURE 44
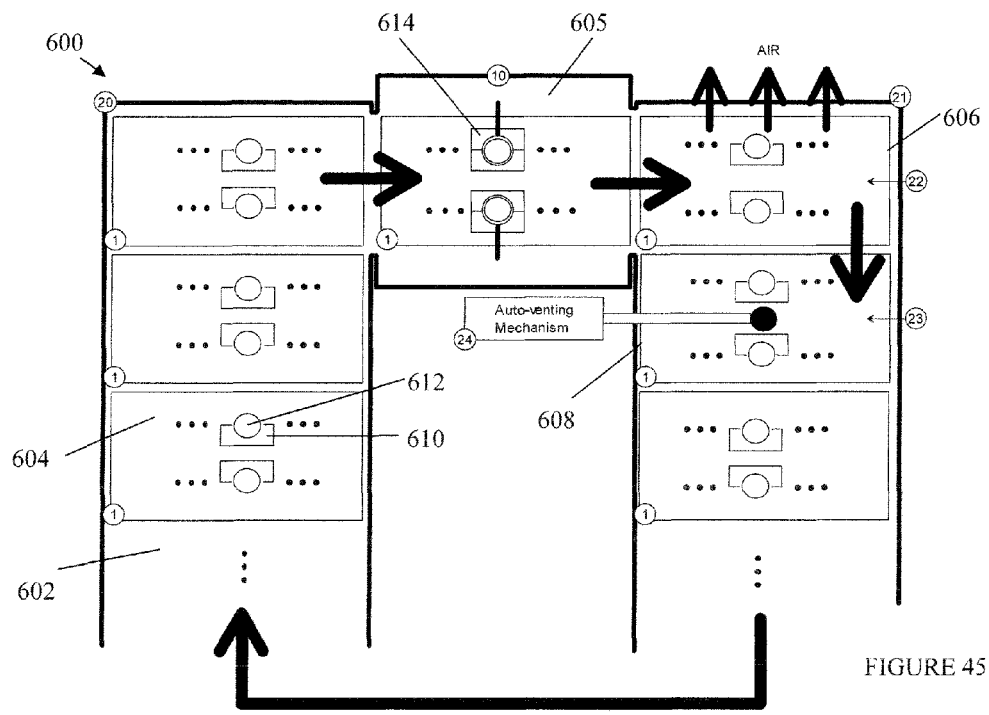
FIGURE 45

AUTOMATED MICROWAVE SAMPLE DIGESTION SYSTEM

CROSS-REFERENCE TO RELATED APPLICATIONS

This application claims priority under 35 U.S.C. §119(e) from U.S. Provisional Patent Application No. 61/304,387, filed on Feb. 12, 2010, the contents of which are hereby incorporated by reference.

TECHNICAL FIELD

The present application relates to the field of sample holder arrangements and systems used in digestion and/or extraction for processes such as analytical spectroscopy and chromatography.

BACKGROUND

In order to perform digestion of a sample, the sample is usually placed in an open-ended recipient which is then closed and heated in a microwave oven. Some digestion systems only allow the heating of a single sample at a time and therefore a single sample holder is used. This practice is particularly time-consuming.

Other digestion systems allow several samples to be concurrently heated and so a multi-sample holder is used. These types of sample holders are usually generic racks that receive multiple open-ended recipients, such as test tubes.

For some digestion processes, heating may result in a large excess pressure in the recipient. To prevent damage or explosion, a valve is provided that automatically opens if a given internal pressure exceeds a threshold. Special sealing caps are used on the open-ended recipient to provide this function. However, having to manipulate such a sealing cap for each sample recipient is also time-consuming.

Therefore, there is a need for an improved system that is adapted for the specific needs of a digestion process for multiple samples concurrently.

SUMMARY

In accordance with a broad aspect, there is provided an automated heating system for heating a sample contained in a sample holder, comprising: a heating chamber having at least one opening and adapted to receive the sample holder; a microwave generator in microwave transfer communication with the heating chamber; a conveyor extending into the heating chamber and adapted to receive and transport the sample holder into and out of the heating chamber; at least one microwave barrier movable between an open position to allow access to the heating chamber and a closed position to prevent microwaves from leaking out of the heating chamber when the microwave generator is activated; and a control unit for controlling the microwave generator and the conveyor.

In some embodiments, the automated heating system further comprises a cooling station downstream from the heating chamber. In yet other embodiments, the automated heating system further comprises a venting station downstream from the cooling station. A conveyor may be used to connect the heating chamber, the cooling station, and the venting station together. An identification reader may be used to identify a given sample in a sample holder.

In one embodiment, the term "sample" refers to a mixture of material to be decomposed and at least one chemical decomposition reagent. In another embodiment, the term "sample" refers only to the material to be decomposed. While the sample recipients may sometimes be referred to as "tubes", it should be understood that they should not be limited to circular in shape. In addition, the term "digestion" should be exchangeable with the term "extraction" throughout the description.

BRIEF DESCRIPTION OF THE DRAWINGS

FIG. 43 is a block diagram illustrating a rectangular microwave cavity, in accordance with an embodiment;

FIG. 44 is a block diagram illustrating a circular microwave cavity provided with a protective element, in accordance with an embodiment;

FIG. 45 is a block diagram of an automated digestion system provided with a mini cavity microwave oven, in accordance with an embodiment;

It will be noted that throughout the appended drawings, like features are identified by like reference numerals.

DETAILED DESCRIPTION

Figure 1:
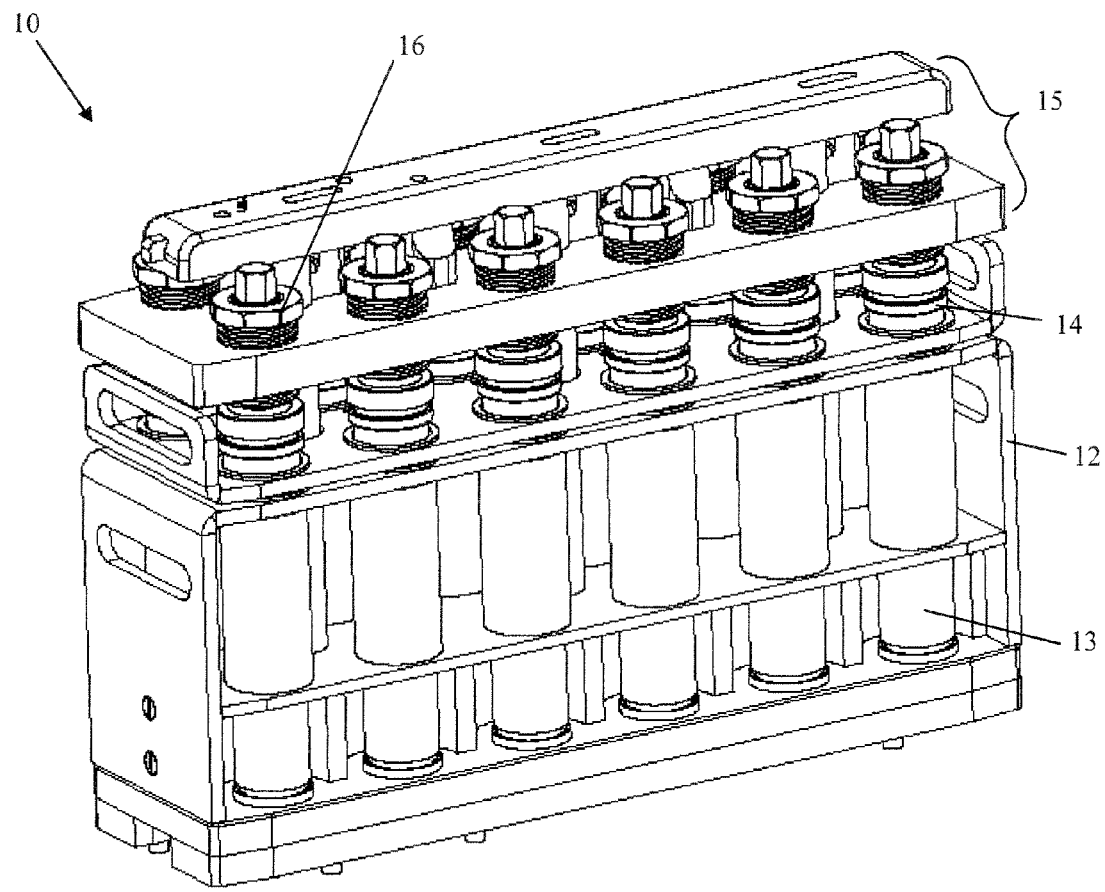
FIG. 1 is a perspective view of a sample holder system, in accordance with an embodiment.

FIG. 1 illustrates one embodiment of a sample holder system 10 ready to be used for decomposition or extraction of a sample material. Sample holder system 10 comprises a rack 12, sample tubes 13 with sealing caps 14, a rack cover 15 and compression caps 16. The material to be extracted or decomposed is placed inside the sample tubes 13 with chemical decomposition agents such as acids, for example. The rack 12 is used to maintain the sample tubes 13 in an upright position. The sealing caps 14 hermetically close the opening of the tubes 13. The compression caps 16 are secured in the rack cover 15. The rack cover 15 with the compression caps 16 secured therein is placed on top of the rack 12 so that the compression caps 16 allow an exhaust of gas when the internal pressure in the tubes 13 exceeds a predetermined threshold value.

The assembly of the compression cap 16 and the sealing cap 14 forms a pressure-relief valve and the rim of a tube 13 is the seat of the pressure-relief valve, whereby excess gas can be evacuated from the tube 13. The compression cap 16 is adapted to allow the opening of the pressure-relief valve when the internal pressure within the tube 13 exceeds the predetermined threshold value.

While FIG. 1 refers to a sample holder arrangement 10 having twelve tubes 13, twelve sealing caps 14 and twelve compression caps 16, it should be understood that the number of these pieces is exemplary only. The sample holder system could be adapted to receive six tubes, twenty tubes, or any other suitable number of tubes.

Figure 2:
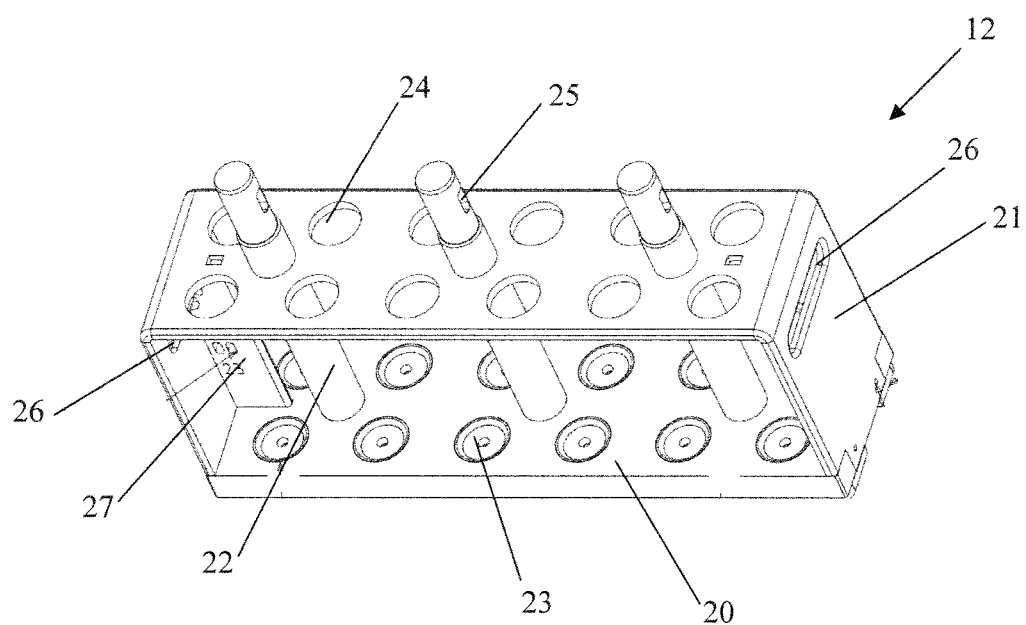
FIG. 2 is a perspective view of a rack of the sample holder system of FIG. 1, in accordance with an embodiment.

Referring concurrently to FIGS. 1 and 2, in one embodiment, the rack 12 has a base 20, a support plate 21 and three studs 22 as illustrated in FIG. 2. The number of studs 22 is exemplary only. The base 20 presents twelve recesses 23. The support plate 21 is U-shaped and comprises twelve apertures 24. Each aperture 24 is positioned on top of and in line with a corresponding recess 23 and the combination of a recess 23 with a corresponding aperture 24 allows a tube 13 to be maintained in the upright position. The recesses 23 and the apertures 24 are sized as a function of the dimensions of the tubes 13, as the tubes will be received therein. The studs 22 each have a slot 25. The studs 22 and their corresponding slots 25 allow the rack cover 15 to be releasably secured on top of the rack 12. The support plate 21 is also provided with a handle 26 on each side. The handles 26 allow an easy transportation of the rack 12. In one embodiment, the central stud is D-shaped at the top to ensure that the rack cover 15 and a transport plate 126 (FIG. 18) are correctly oriented.

The studs 22 may be replaced by any system which allows the rack cover 15 to be releasably secured to the rack 12. For example, the studs 22 may be replaced by a plate provided with notches to secure the rack cover 15.

Figure 3:
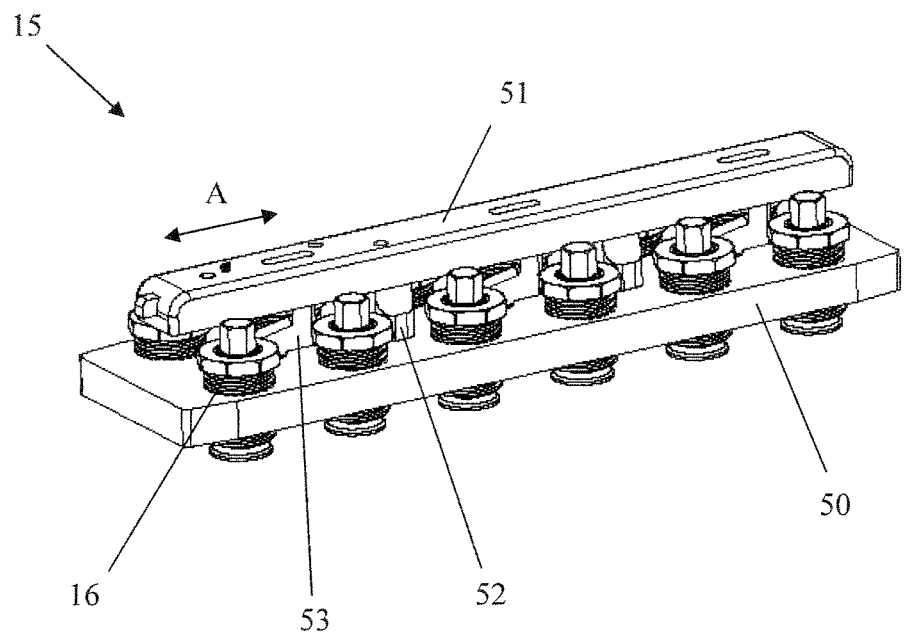
FIG. 3 is a perspective view of a rack cover of the sampled holder of FIG. 1 with compression caps attached thereto, in accordance with an embodiment.

FIG. 3 illustrates one embodiment of the rack cover 15 in which the compression caps 16 are secured. The rack cover 15 comprises a cap-receiving plate 50 and a clamping bar 51 which are interconnected to one another through supporting brackets 52. The clamping bar 51 comprises three slot members 53 which are designed to slide into the slots 25 of the studs 22 (FIG. 2) in order to removably secure the rack cover 15 to the rack 12. The slot members 53 are located according to the location of the slots 25 of the studs 22. The clamping bar 51 slides relatively to the securing brackets 52 and the cap-receiving plate 50, according to direction A. This translation movement allows the slot members 53 to be inserted into the slots 25. When the clamping bar 51 is in a closed position (i.e., when the rack cover 15 is attached to the rack 12), the slot members 53 are locked to the studs 22. When the clamping bar 51 is in an opened position (i.e., when the rack cover 15 lies on the rack 12 but the slot members 53 are not interlocked into the slots 25), the slot members 53 are not in line with the studs 22, whereby the rack cover 15 may be separated from the rack 12 by being lifted away.

Figure 4:
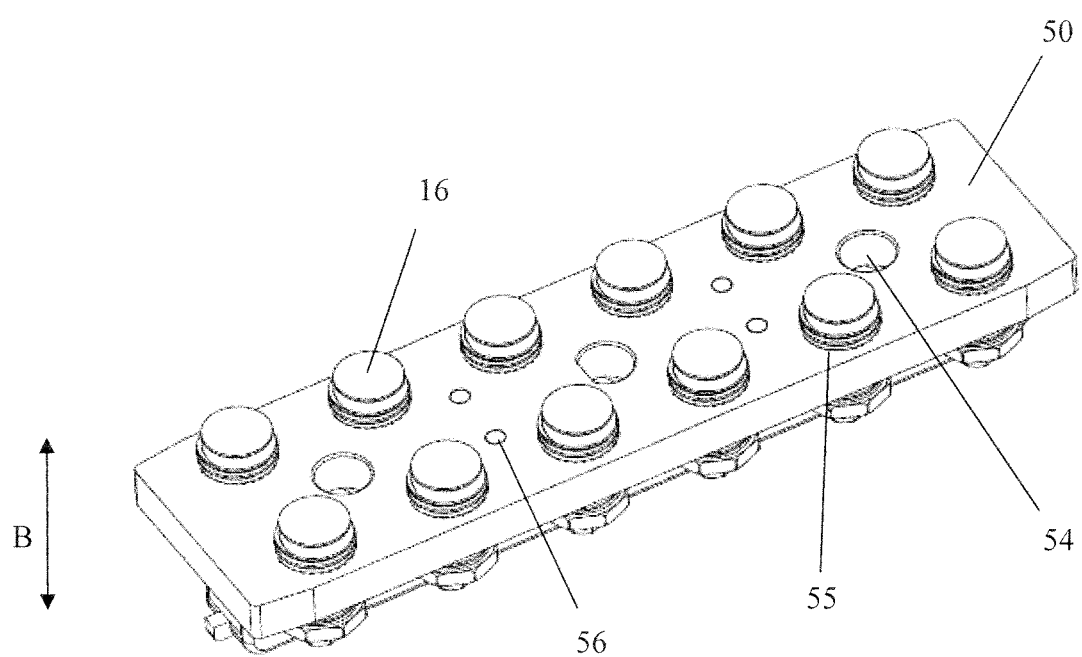
FIG. 4 is a bottom perspective view of a cap-receiving plate of the rack cover of FIG. 3 with compression caps attached thereto, in accordance with an embodiment.

FIG. 4 illustrates one embodiment of the cap-receiving plate 50 in which the compression caps 16 are threadingly engaged. The cap-receiving plate 50 is provided with two types of apertures, namely stud-receiving apertures 54 and cap-receiving apertures 55. The stud-receiving apertures 54 are provided in a number equal to that of the studs 22 and they are located according to the location of studs 22 in rack 12. The dimensions of the stud-receiving apertures 54 are chosen according to the dimensions of the studs 22. When the rack cover 15 is installed on top of the rack 12, the studs 22 are inserted into the stud-receiving apertures 54, in a direction corresponding to B. The studs are removable from the stud-receiving apertures in order to change the studs of given height for studs of a different height, thereby accommodating tubes of a different height.

The cap-receiving apertures 55 are designed to receive the compression caps 16. They have a thread (not visible in FIG. 4) so that the compression caps 16 are screwed therein. The cap-receiving plate 50 also has fixing holes 56 which are used to fixedly secure the supporting brackets 52 by way of bolts, for example. Alternatively, the supporting brackets can be attached to the cap-receiving plate 50 using an adhesive, or any other removable or permanent mechanical connector. In one embodiment, the compression caps 16 are permanently secured to the cap-receiving plate 50 while in another embodiment, they are releasably secured.

Figure 5:
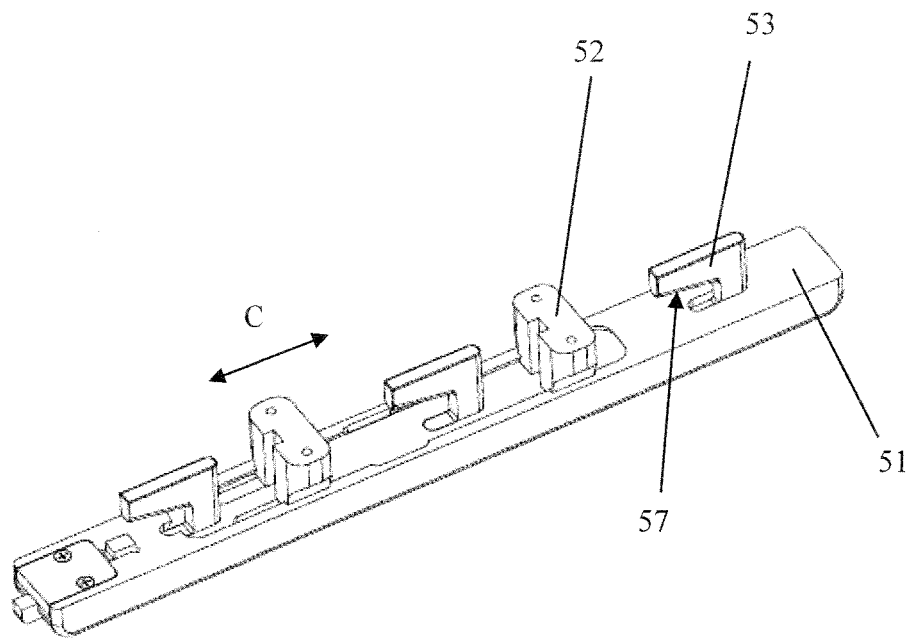
FIG. 5 is a bottom perspective view of a clamping bar of the rack cover of FIG. 3, in accordance with an embodiment.

FIG. 5 presents a bottom view of one embodiment of the clamping bar 51 on which the supporting brackets 52 are attached. The supporting brackets 52 can be translated along the clamping bar 51 as illustrated by arrow C. This relative movement between the supporting brackets 52 and the clamping bar 51 (illustrated by direction A in FIG. 3) allows the slot members 53 to be slid into the slots 25 of the studs 22. In one embodiment, the slot members 53 may have an L shape and be designed with a wedged surface 57 for improving the securing of rack cover 15 to rack 12.

Figure 6:
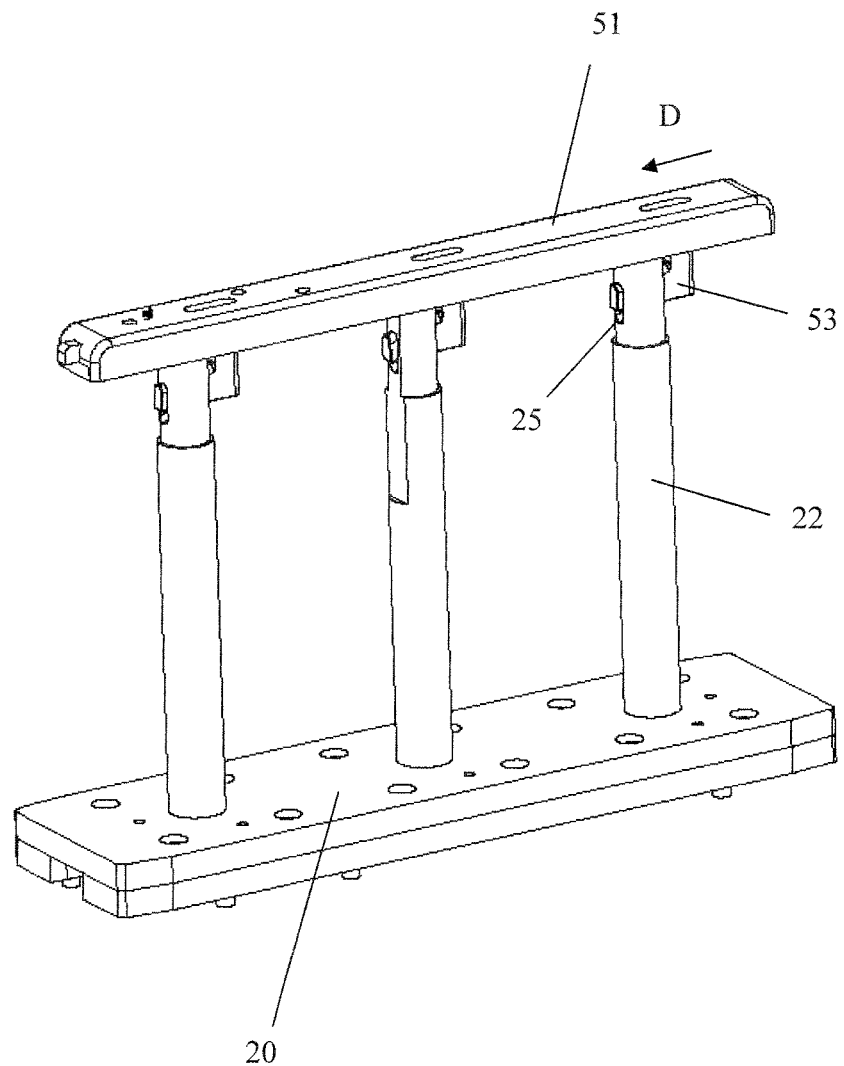
FIG. 6 is a perspective view illustrating the securing of the clamping bar of FIG. 5 to the rack of FIG. 2, in accordance with an embodiment.

FIG. 6 illustrates how the rack cover 15 is secured on the rack 12. For simplification purposes, only the base 20 and the studs 22 are represented for the rack 12 and only the clamping bar 51 is represented for the rack cover 15 in FIG. 6. The slot members 53 slide into the slots 25 of the studs 22 according to direction D as a result of a translation of the clamping bar 51, thereby allowing the rack cover 15 to be locked to the rack 12.

Figure 7:
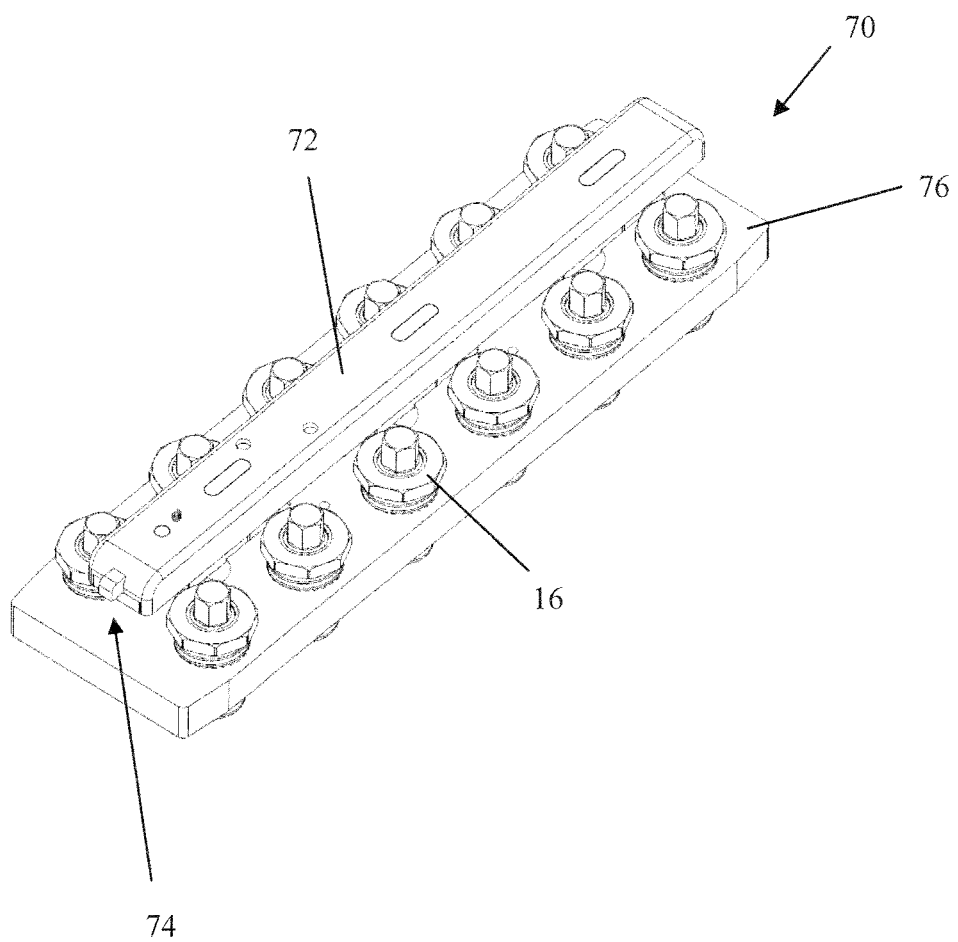
FIG. 7 is a perspective view of a rack cover provided with a safety mechanism, in accordance with an embodiment.
Figure 8A:
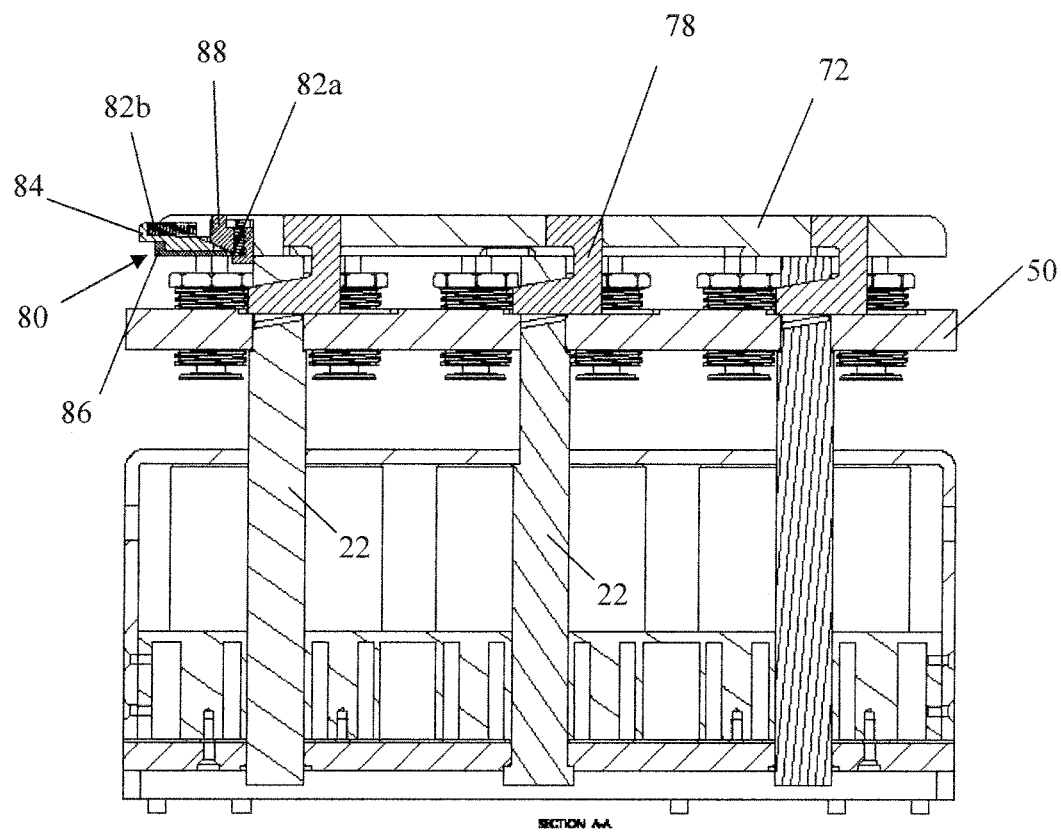
FIG. 8a is a partial side view of the rack cover of FIG. 7 secured to a rack, in accordance with an embodiment.
Figure 8B:
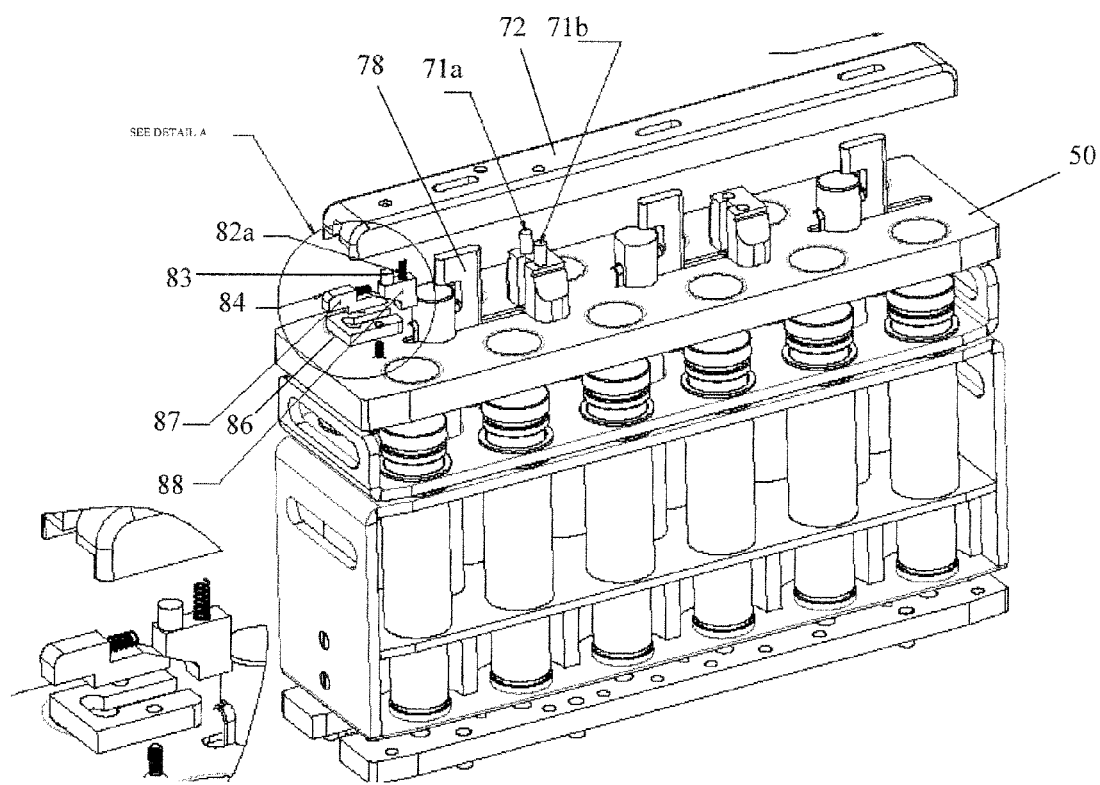
FIG. 8b is a blown-up perspective view of the rack cover of FIG. 7, showing the safety mechanism in more detail, in accordance with an embodiment.

FIG. 7 illustrates one embodiment of a rack cover 70 securable on top of the rack 12 and comprising a clamping bar 72 provided with a safety mechanism 74 for preventing the clamping bar 72 from unlocking from the studs 22 of the rack 12. Similarly to the rack cover 15 illustrated in FIG. 3, the rack cover 70 comprises a cap-receiving plate 76 having cap-receiving apertures in which compression caps 16 are screwed. The clamping bar 72 is translationally secured to the cap-receiving plate 76 in order to slide slot members 78 into respective slots of the rack studs 22, as illustrated in FIG. 8a. The clamping bar 72 comprises a recess 80 in which the safety mechanism 74 is secured. The safety mechanism 74 comprises a locking member 84 provided with an aperture 86 in which a spring 82b is inserted and an abutment member 88 for mating with the locking member 84. The abutment member 88 also has a spring 82a and a pin 83. Pin 83 (see FIG. 8b) moves up and down and is completely engaged when the clamping bar 72 is locked. Pins 71a and 71b act as visual indicators of a locking and unlocking of the clamping bar 72. In this embodiment, one of the pins 71a, 71b is green while the other one is red. Only the red one is visible when the clamping bar 72 is locked. Only the green one is visible when the clamping bar 72 is unlocked. Other ways of providing visual indication of a locked or unlocked state will be readily apparent to those skilled in the art.

The safety mechanism 74 is movable between a closed position and an opened position. The abutment member 88 mates with the locking member 84 and is made of flexible material such as plastic for example, in order to bias the safety mechanism 74 in the closing position. The abutment member 88 abuts against the bottom surface of the clamping bar 72 and is positioned in compression to exert a downward force on the rear end of the locking member 84 via the spring 82a. As a result of the downward force, the rear end of the abutment member 88 engages the stud 22 when the safety mechanism 74 is in the closed position, thereby preventing the slot members 78 from dislodging from the stud slots. By exerting a lateral force on the front end of the locking member 84, the safety mechanism 84 is brought into the opening position which allows the clamping bar 72 to rearly slide in order to dislodge the slot members 78 from the stud slots. As a result of a lateral force exerted on the front end of the locking member 84, pin 83 is released and moves upwardly, thereby disengaging the abutment member 88 from the stud 22.

While the present description refers to an abutment member 88 for biasing the safety mechanism 74 in the closing position, it should be understood that any adequate mechanical compression device may be used. For example, a coil spring may be inserted in compression between the rear end of the locking member and the bottom of the clamping bar 72 to directly exert a downward force on the rear end.

Figure 9A:
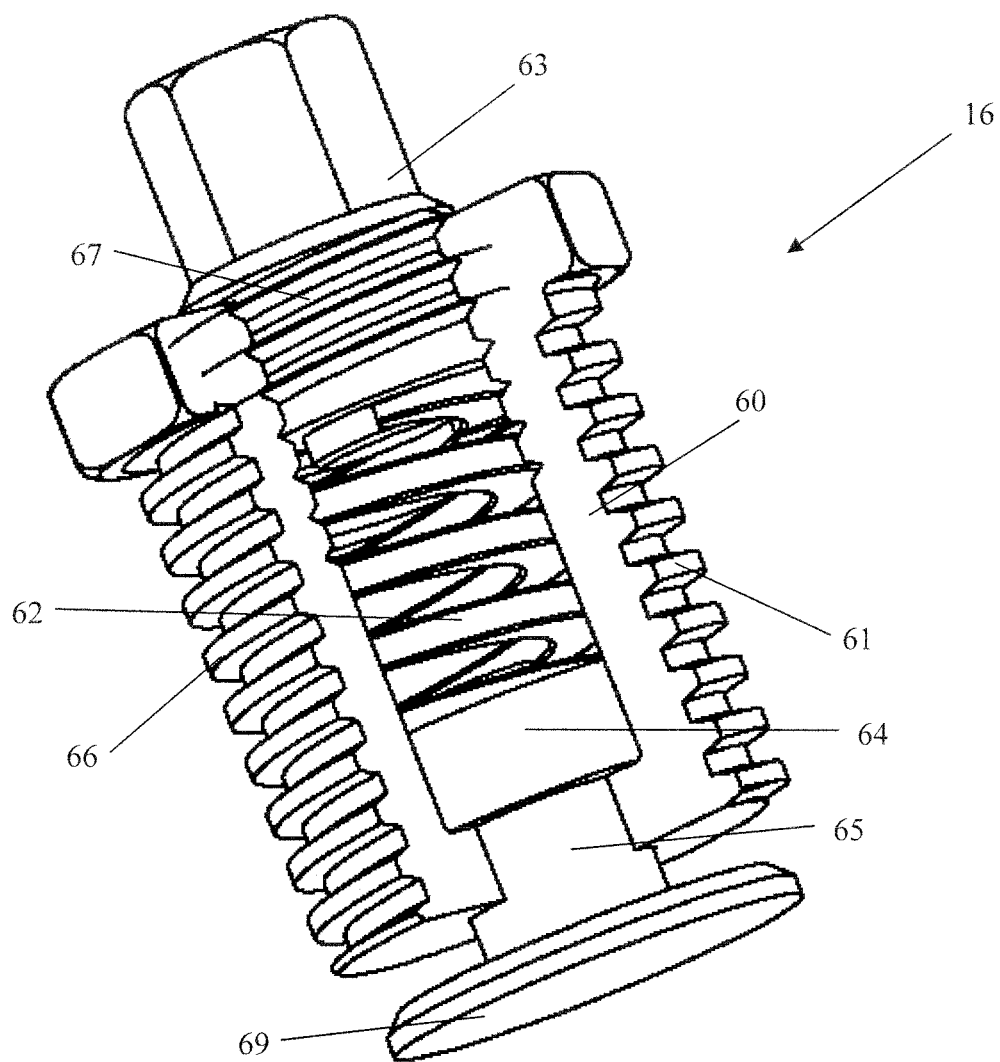
FIG. 9a is a partially sectional perspective view of a compression cap to be secured in the cap-receiving plate of FIG. 4, in accordance with an embodiment.

FIG. 9a illustrates one embodiment of the compression cap 16. The compression cap 16 comprises a cap casing 60 which is a hollow cylinder having a screw thread 61 on its external surface in order to be screwed into the cap-receiving apertures 55 of the cap-receiving plate 50. The compression cap 16 comprises a chamber accommodating a helical spring 62, a pressure-adjusting bolt 63 and a piston 64, and an aperture adapted to receive a pressure arm 65. The chamber and the aperture are connected so that the pressure arm 65 travels through the aperture and part of the chamber.

The pressure arm 65 is secured to the piston 64 so as to be biased by the spring 62 to exert pressure on the sealing caps 14. For example, the pressure arm 65 may present a screw thread on part of its external surface and can be screwed into the piston 64, which has a threaded cavity for receiving the pressure arm 65. Alternatively, the pressure arm 65 and piston 64 can be integrated into a single piston piece. The spring 62 is placed into the cap casing 60 in compression so that a biased force is applied by the spring 62 on the piston 64.

The spring 62 may be of any shape and dimensions. While the compression cap 16 comprises a spring 62 to apply a biased force on the piston 64 and to prevent an exhaust of gas from the tube 13 before the internal pressure in the tube 13 has reached a threshold value, it should be understood that the spring 62 can be replaced by any piece that applies a biased force on the piston 64.

In one embodiment, the spring 62 is made from metal and covered by an acid-resistant plastic sleeve to protect the spring 62 from acid vapours and avoid corrosion.

In one embodiment, the pressure-adjusting bolt 63 has a fixed position and no adjustment of the biasing force of the spring 62 is possible. In this case, the pressure adjusting bolt 63 may be integral with the casing 60 of the compression cap 16.

Figure 9B:
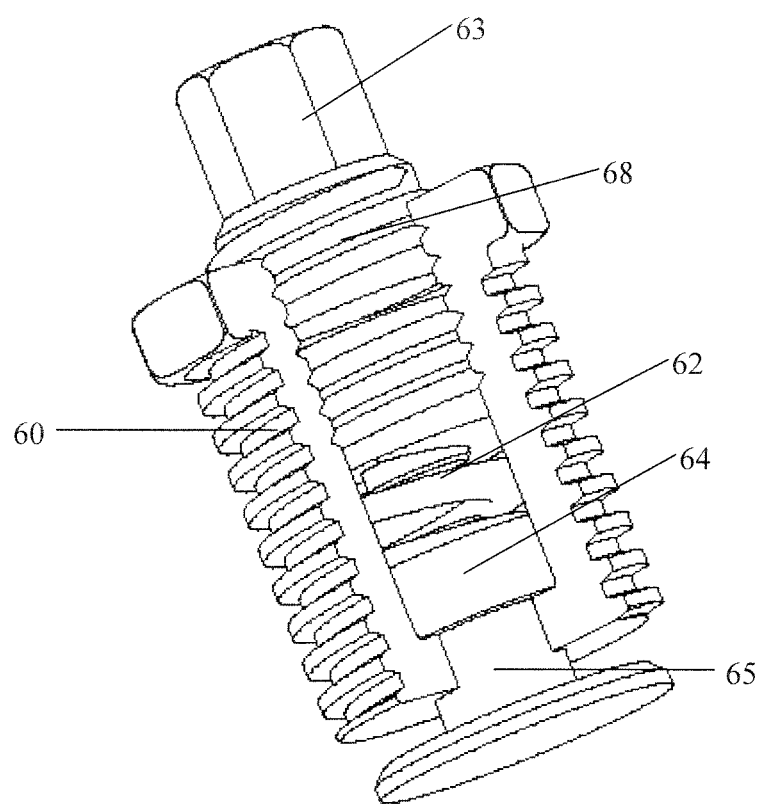
FIG. 9b is another embodiment of a partially sectional perspective view of a compression cap, with a lock washer added.
Figure 9C:
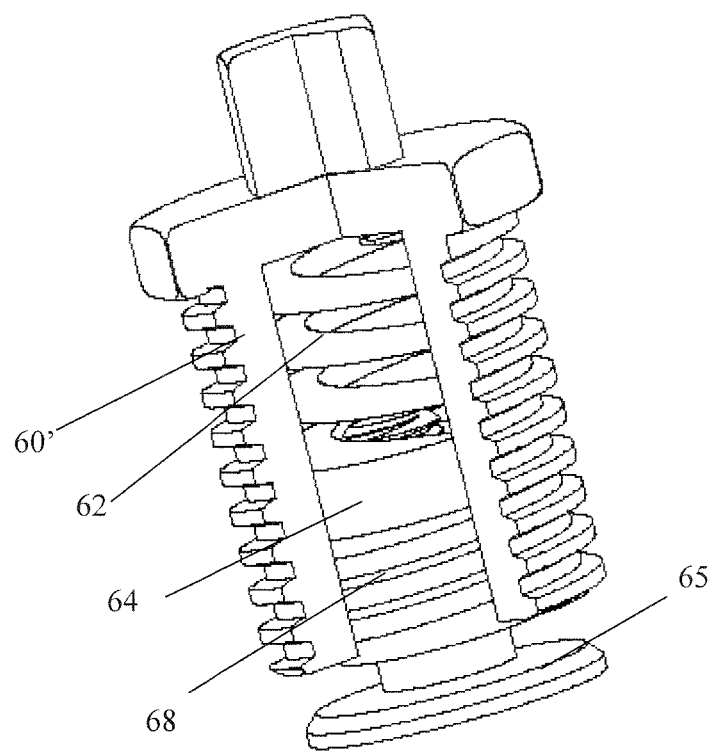
FIG. 9c is yet another embodiment of a partially sectional perspective view of a compression cap, with the order of parts reversed.

FIG. 9b is another embodiment of the compression cap 16. In this embodiment, a lock washer 68 has been added. This will be explained in more detail with reference to FIG. 10b. FIG. 9c is yet another embodiment of the compression cap 16, where the order of the various parts has been reversed. This will be explained in more detail with reference to FIG. 10c.

Figure 10A:
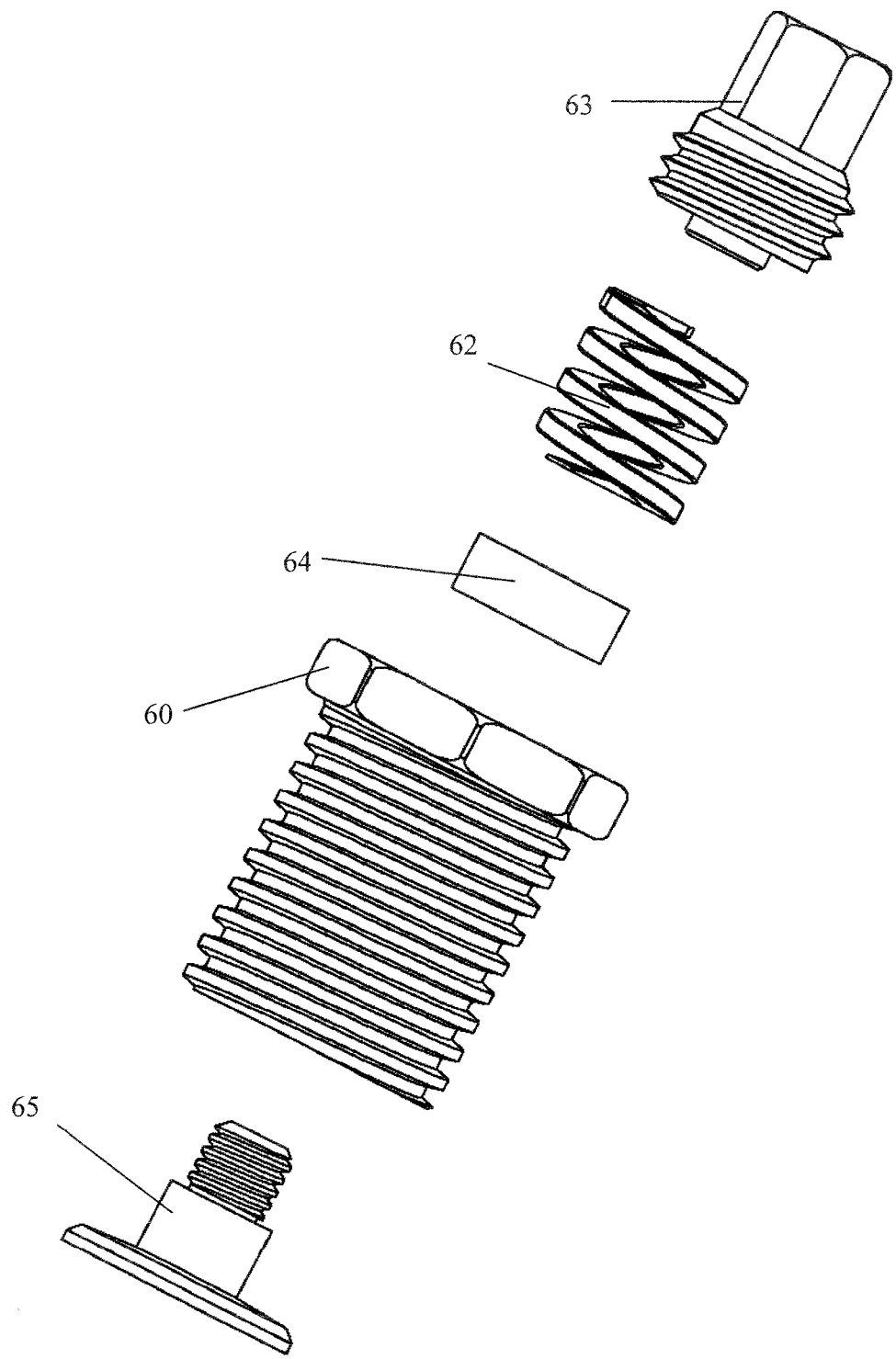
FIG. 10a is an exploded perspective view of the compression cap of FIG. 9a, in accordance with an embodiment.
Figure 10B:
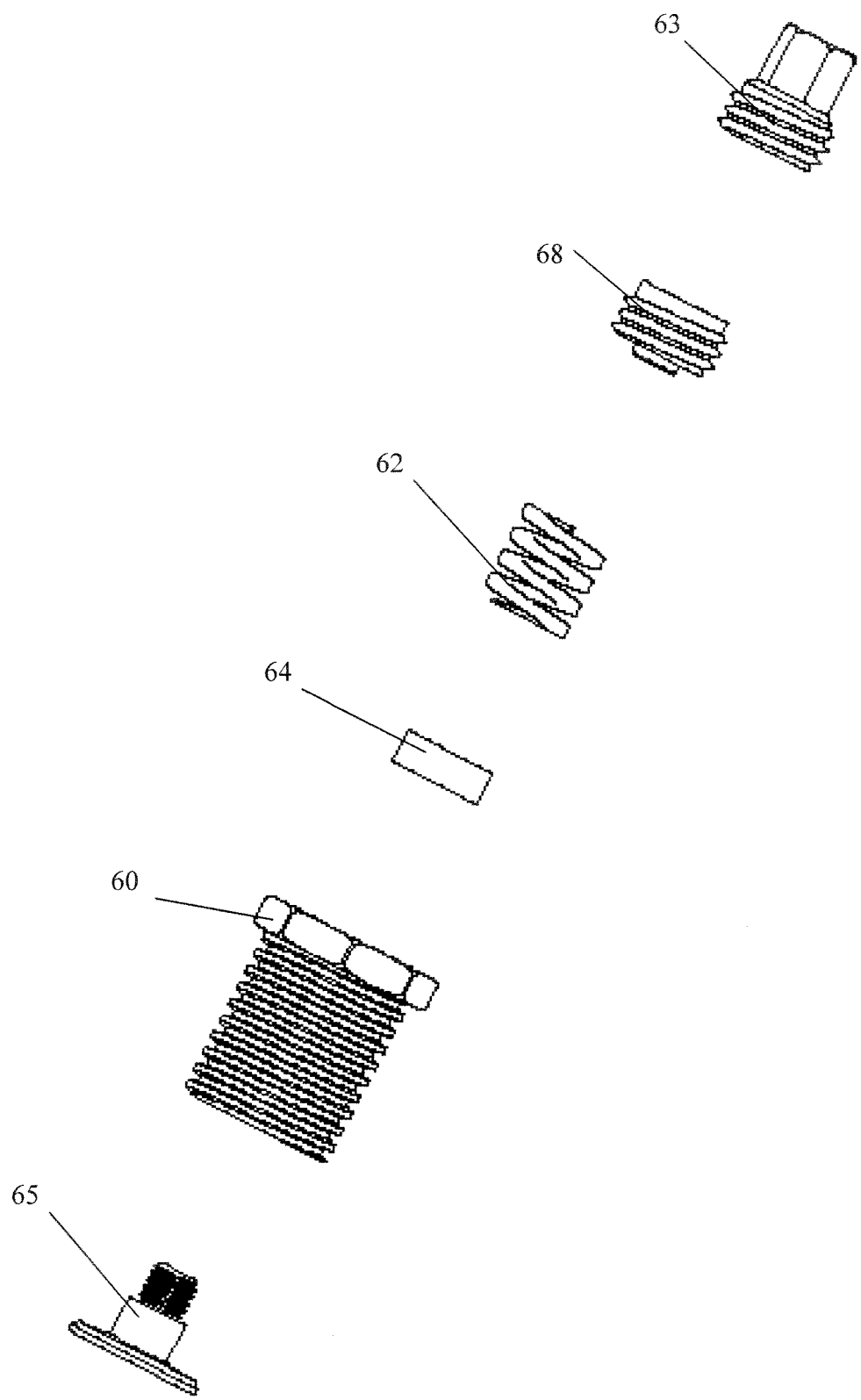
FIG. 10b is an exploded perspective view of the compression cap of FIG. 9b, in accordance with an embodiment.
Figure 10C:
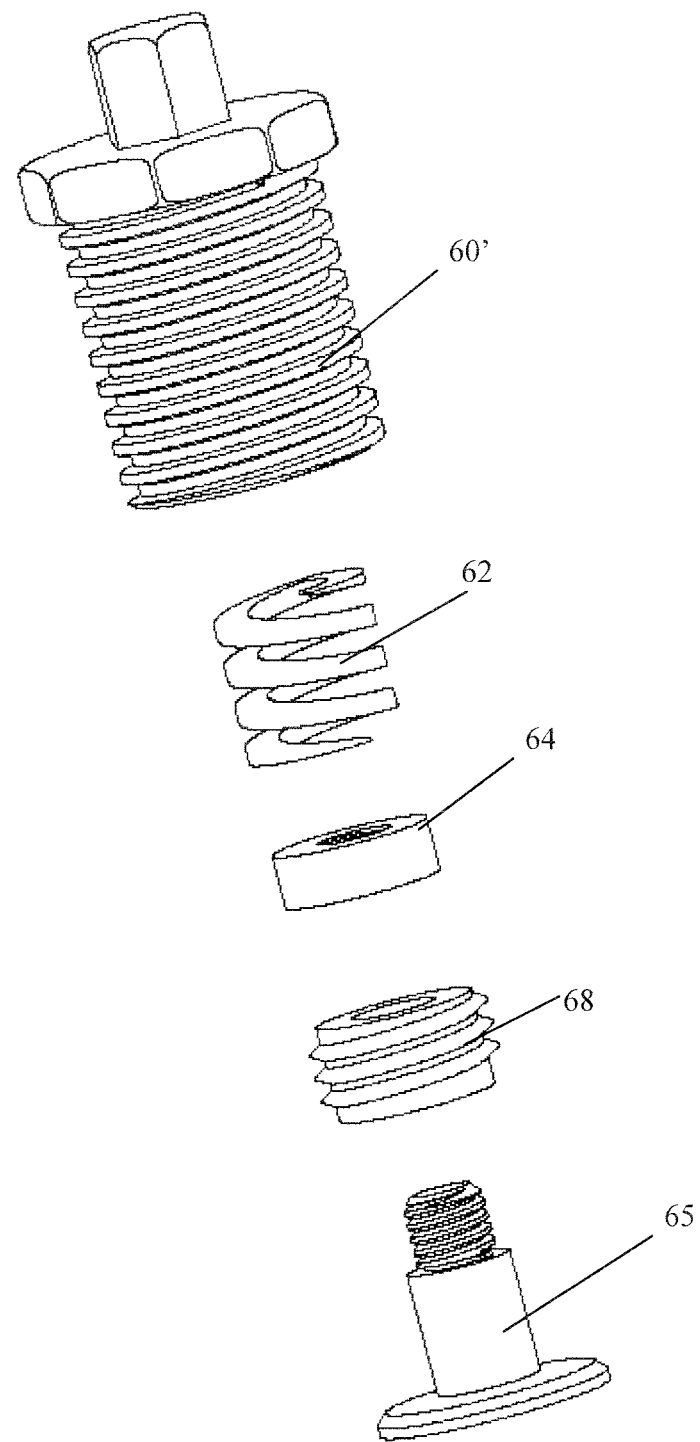
FIG. 10c is an exploded perspective view of the compression cap of FIG. 9c, in accordance with an embodiment.

FIG. 10a illustrates an embodiment of the cap casing 60 without the pressure arm 65. The cap casing 60 has thread 66 on part of its internal surface in the chamber. The pressure-adjusting bolt 63 has a screw thread 67 on its external surface. The screw thread 67 corresponds to the thread 66 so that the pressure-adjusting bolt 63 can be screwed into the cap casing 60. FIG. 10b illustrates another the embodiment shown in FIG. 9b, whereby an additional lock washer 68 is present. The lock washer 68 is installed after the spring 62 and is screwed into the barrel of the cap casing 60 until the spring 68 reaches its appropriate tension. This level of tension is the maximum pressure on the compression cap 16 of the vessel that the safety mechanism must resist in order that the cap 16 does not release pressure from the vessel. FIG. 10c illustrates the embodiment shown in FIG. 9c. The cap casing 60' is a combination of cap casing 60 and pressure adjusting bolt 63. The spring 62, piston 64, lock washer 68, and pressure arm 65 are all the same as in the embodiment illustrated in FIG. 10b, but in a different order. This allows calibration to be done from the bottom of the cap (i.e. pressure arm 65) and adjustment of the cap casing 60' from the top does not affect this calibration.

It should be noted that the shape and dimensions of the compression caps 16 may vary. For example, the compression caps 16 may have a square shape and the apertures 24 may be adapted to receive the compression caps 16. The compression caps 16 may also be secured to the rack cover 15 by way of screws or clamps for example.

When it is screwed into the cap casing 60, the pressure-adjusting bolt 63/lock washer 68 compresses the spring 62. It results in an increased biased force exerted by the spring 62 on the piston 64. When the internal pressure increases in the tube 13, an upward vertical force is applied on the piston 64 through the sealing cap 14 and the pressure arm 65. The piston 64 cannot move as long as the biased force applied by the spring 62 is superior or equal to the upward vertical force resulting from the pressure increase in the tube 13. The internal pressure in the tube 13 which creates an upward force applied on the piston 64 that is equal to the biased force applied by the spring 62 on the piston 64 corresponds to a threshold pressure. This threshold pressure can be controlled by adjusting the position of the pressure-adjusting bolt 63/lock washer 68 within the cap casing 60.

When the internal pressure in the tube 13 is inferior to the threshold pressure, the pressure-relief valve system constituted of the compression cap 16, the sealing cap 14 and the rim of a tube 13 is in a closed position and the tube 13 is hermetically closed. When the internal pressure in the tube 13 exceeds the threshold pressure, the pressure-relief valve system is in an open position and gas can exhaust from the tube 13. This relief of gas limits the internal pressure in the tube 13 and prevents damage to or explosion of the tube 13. When the internal pressure goes back below the threshold pressure, the pressure-relief valve system hermetically closes back the tube 13 since the biased force applied by the spring 62 is superior to the upward force created by the internal pressure of the tube 13.

In one embodiment, the compression cap 16 and the sealing cap 14 form a same and single piece. In this case, a disk 69 of the pressure arm 65 has a shape and a size adapted to act as a sealing cap in order to close the tube 13. Having a sealing cap and a compression cap as two different pieces enables the compression cap 16 to be used with different sealing caps 14 independently of the shape and dimensions of the sealing cap 14.

Figure 11A:
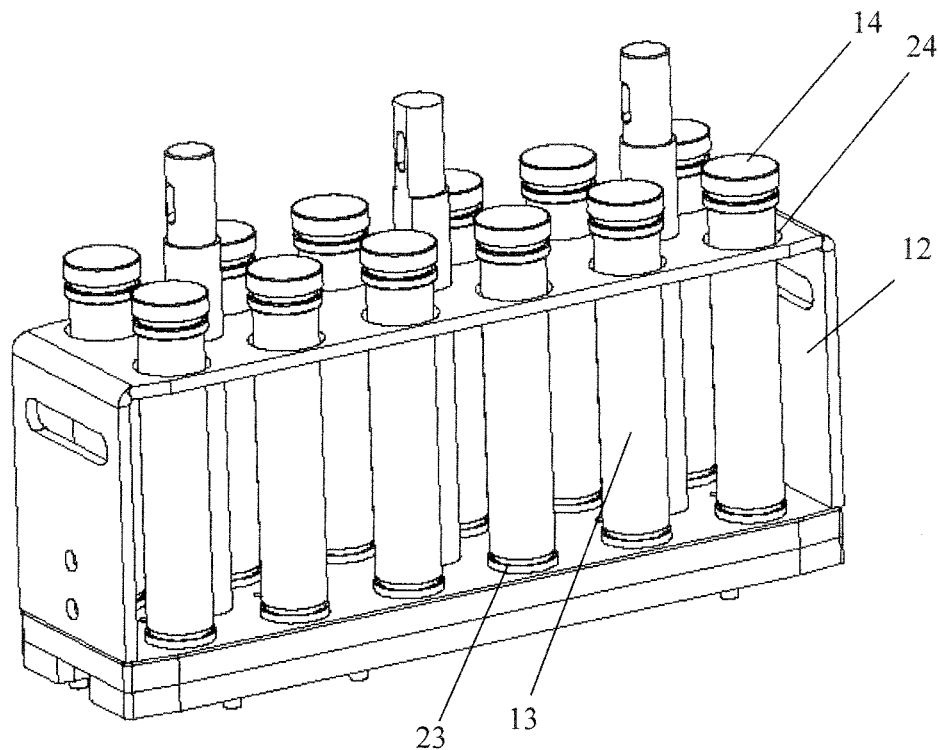
FIG. 11a is a perspective view of the rack of FIG. 2 accommodating tubes closed by sealing caps, in accordance with an embodiment.
Figure 11B:
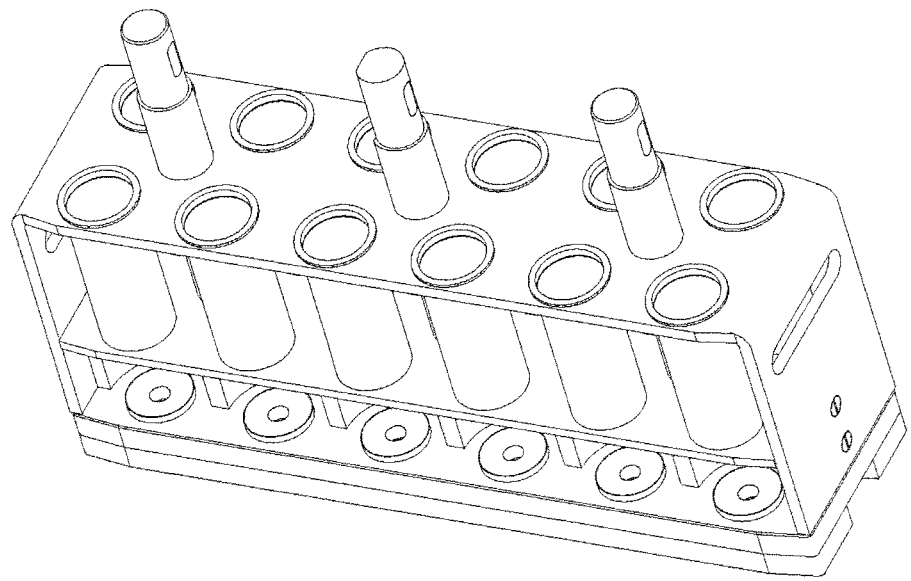
FIG. 11b is a perspective view of the rack without any tubes, with microwave reflecting cylinders, in accordance with an embodiment.

FIG. 11a illustrates one embodiment of the installation of the tubes 13 in the rack 12. The material to be extracted or decomposed is placed inside the tubes 13 with appropriate chemical decomposition agents. The tubes 13 are positioned through the apertures 24 and rest on the recesses 23. The sealing caps 14 are positioned on top of the tubes 13. The compression caps 16 are threadingly locked into the apertures 55 of the rack cover 15 as illustrated in FIG. 4. The compression caps 16 are chosen in accordance with a desired threshold pressure. If an adjustment of the threshold pressure is required, the location of the pressure-adjusting bolts 63/lock washer 68 within the cap casings 60 can be adjusted. FIG. 11b illustrates a different embodiment for the rack, with microwave reflecting cylinders (explained in more detail below).

The rack cover 15 with the compression caps 16 thereon is positioned on top of the tubes 13 in the rack 12. During the positioning of the rack cover 15 on top of the tubes 13, the studs 22 are threaded into the apertures 54 of the rack cover 15 and the cap-receiving plate 50 slides down along the studs 22 in the direction of arrow B (FIG. 4). The rack cover 15 with the compression caps 16 secured therein is locked to the rack 12 by inserting the slot members 53 of the clamping bar 51 into the slots 25 of the studs 22. The insertion of the slot members 53 is achieved thanks to a translation movement of the clamping bar 51 in the direction of arrow D (FIG. 6). As indicated above, the middle stud may have a D-shaped slot to provide better orientation between the rack cover and the transport plate.

The insertion of the slot members 53 into the slots 25 exerts a downward force on the rack cover 15 and on the compression caps 16 as they are secured to the rack cover 15. This downward force is transferred to the springs 62 of the compression caps 16 via the bolts 63 or lock washer 68. The downward force does not add any extra force adds a further compression to the springs 62, which increases the biasing force exerted by the springs 62 on the pistons 64. The downward force resulting from the locking of the rack cover 15 allows the tubes 13 to be hermetically closed. As a result, the threshold pressure at which the relief of gas occurs is the pressure corresponding to an upward force equal to the biasing force exerted by the springs 62 on the pistons 64 in addition to the (no extra force) downward force resulting from the insertion of the slot members 53 into the slots 25.

Having the compression caps 16 already installed on the rack cover 15 before securing it to the rack 12 allows a gain in time, as each compression cap 16 does not have to be screwed and adjusted independently. It also allows automation of the assembly of the sample holder system 10. When the sample holder system 10 is assembled, the cap-receiving plate 50 is at a predetermined distance from the base 20. This predetermined distance enables the compression caps 16 to lie on the sealing caps 14 so that the tubes 13 are hermetically closed when the slot members 53 are inserted into the slots 25. If a small adjustment is required, this can be achieved by turning the bolt 63. Once the assembly is finished, the sample holder system 10 is ready to be placed into heating equipment, such as a microwave oven, when heat is required for decomposition of the material.

In order to dismantle the sample holder system 10, the slot members 53 are dislodged from the slots 25 by translating the clamping bar 51 in the opposite direction of arrow D (FIG. 6). The rack cover 15 is removed from the rack 12 by upwardly translating the rack cover 15 along the studs 25 of the rack 12. The tubes 13 can then be removed from the rack 12.

In one embodiment, the sample holder system 10 is placed into a conventional or microwave oven for decomposition of the sample material. After being taken out from the oven, the samples are cooled using air blowers for example. After a predetermined cooling time, the rack cover 15 is unlocked by translating the clamping bar 51 in the opposite direction of arrow D (FIG. 6), thereby dislodging the slot members 53 from the slots 25. This allows for an auto-venting of all of the tubes 13.

In one embodiment, the rack 12 is provided with at least one temperature sensor positioned below the recesses 23 in order to measure the temperature of the tubes 13. In this case, the rack cover 15 is unlocked when the temperature of the sample material contained within the tubes 13 is below a threshold value. In one embodiment, the rack 12 is provided with a single temperature sensor for measuring the temperature of a single tube 13, namely a reference tube, and the rack cover 15 is unlocked when the temperature of the sample material within the reference tube is below the temperature threshold.

The different pieces of the sample holder system 10 may be made of heat-resistant materials if a conventional oven is used. If the heating equipment is a microwave oven, the different pieces of the system 10 may be chosen to be compatible with microwave heating. In one embodiment, the different pieces of the sample holder 10 are made from an acid-and-microwave resistant material such as plastic for example.

In one embodiment, at least the studs 22 are removable from the rack 12 so that studs of different height may be removably secured to the base 20. The height of the studs 22 may be chosen as a function of that of the tubes 13. For example, studs having a first adequate height may be used with 50 ml sample tubes and studs having a longer adequate height may be used with 75 ml sample tubes. By simply choosing studs having an adequate height, the sample holder 10 can accommodate sample tubes of different heights.

In one embodiment, the rack cover 15 is first secured to the rack 12 and subsequently, the compression caps 16 are individually screwed into the cap-receiving plate 50.

While the description refers to sample tubes 13 to receive the material to be decomposed, it should be understood that any container having any shape and dimensions can be used as a receiving part. In this case, the rack 12 and the sealing caps 14 are adapted to receive the container and to hermetically close the container, respectively.

The sample holder system may be of any shape and size. In particular, any frame adapted to receive the sample tubes 13 can be used and any cover into which the compression caps 16 can be inserted may also be used. While the rack 12 is a hollowed piece, it could be replaced by a block having holes adapted to receive the tubes 13, for example.

Figure 12:
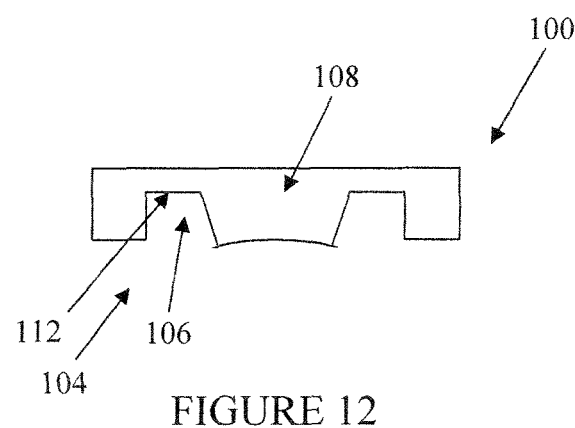
FIG. 12 is a cross-sectional view of a sealing cap, in accordance with an embodiment.
Figure 13:
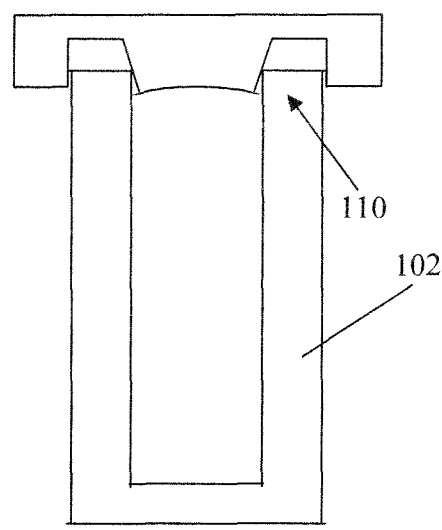
FIG. 13 is a cross-sectional view of a test tube covered by the sealing cap of FIG. 12, in accordance with an embodiment.

FIGS. 12 and 13 illustrates one embodiment of a sealing cap 100 for sealing a cylindrical sample tube 102. The sealing cap 100 has a tube engaging side 104 provided with a circular groove 106 and a central conical protrusion 108. The groove 106 and the protrusion 108 are sized and shaped so that the rim 110 of the sample tube 102 does not abut against the bed surface 112 of the groove 106 when the sealing cap 100 is positioned on top of the tube 102, as illustrated in FIG. 13. Therefore, the tube is not hermetically close when the sealing cap 100 is positioned on top of the tube 102.

The sealing cap 100 is made from a flexible material so that the groove 106 and the conical protrusion 108 may be deformed when the sealing cap 100 is positioned on top of the tube 102 and a downward force is exerted on top of the sealing cap 100. The downward force may be exerted by a compression cap such as compression cap 16 for example. As a result of the downward force, the walls of the groove 106 hermetically engage the rim of the tube 102 to hermetically close the tube 102.

Figure 14:
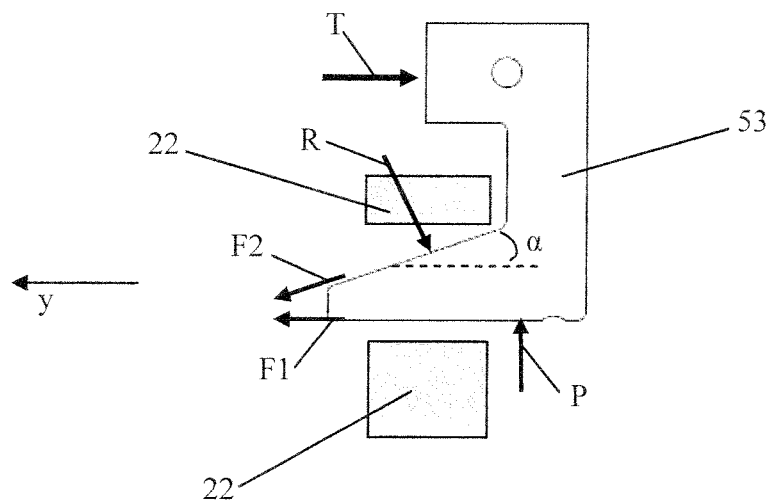
FIG. 14 illustrates forces exerted on a slot member of the clamping bar of FIG. 5 when inserted into a rectangular slot of a stud of the rack of FIG. 2, in accordance with an embodiment.

FIG. 14 illustrates an example of forces in action when a slot member 53 is positioned in a slot 25 of a stud 22. It should be noted that this example is illustrative only and that other scenarios involving same or different forces are also possible. Force T is the force used to push back the slot member 53 out of the slot 25. Force R is the reaction force exerted by the stud 22 on the slot member 53. Forces F1 and F2 are friction forces resulting from the friction of the slot member 53 on the stud 22 when the slot member 53 is pushed back. Force P is the force resulting from the increase of internal pressure in the tubes 13.

Friction force F1 can be expressed as a function of the force P and a coefficient of friction $\mu$ as shown in the following equation:

$$F1 = \mu * P \tag{Eq. 1}$$

The friction force F2 can be expressed as a function of the force R and the coefficient of friction μ as shown in the following equation:

$$F2 = \mu * R \quad \text{(Eq. 2)}$$

Force T is the force resulting from the friction forces F1 and F2 in the y-direction and is given by equation 3:

$$T = \mu * P + R * (\mu * \cos \alpha - \sin \alpha) \quad \text{(Eq. 3)}$$

where α is the angle of the wedge of wedged surface 56 of the slot member 53.

The force R can be expressed as a function of the force P, the coefficient of friction μ and the angle α according to equation 4:

$$R = P / (\cos \alpha + \mu * \sin \alpha) \quad \text{(Eq. 4)}$$

Substituting the force R by equation 4 in equation 3, the force T can be expressed as:

$$T = P * \mu + P * (\mu * \cos \alpha - \sin \alpha) / (\cos \alpha + \mu * \sin \alpha) \quad \text{(Eq. 5)}$$

Equation 6 is a simplified expression of equation 5:

$$T = P * \text{coef}(\mu, \alpha) \quad \text{(Eq. 6)}$$

where $$\text{coef}(\mu, \alpha) = \mu + (\mu * \cos \alpha - \sin \alpha) / (\cos \alpha + \mu * \sin \alpha) \quad \text{(Eq. 7)}$$

Equation 6 shows that the force T is proportional to the force P. As a result, the force T, which is the force used to push back the slot member 53 out of the slot 25, is proportional to the increase of internal pressure in the tube 13 and is also a function of the angle α. Therefore, it is possible to adjust the force T by controlling the angle α.

Figure 15:
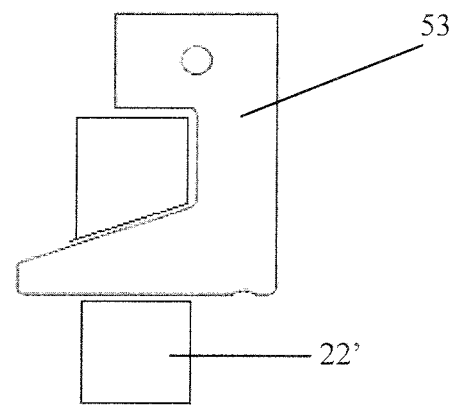
FIG. 15 illustrates a cross-sectional view of a slot member of the clamping bar of FIG. 5 when inserted into a slot having a matching shape, in accordance with an embodiment.

While FIG. 14 illustrates a stud 22 having a rectangular slot, it should be understood that the slot may have any adequate shape. For example, FIG. 15 illustrates a stud 22' provided with a slot having a shape matching that of the slot member 53.

Figure 16:
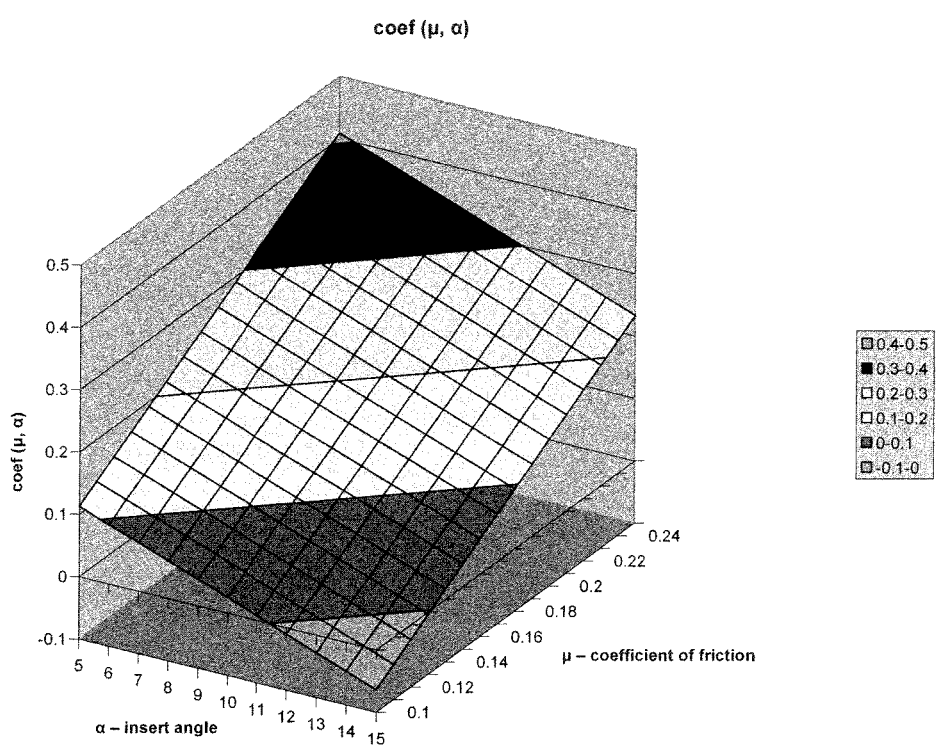
FIG. 16 is a graph of coefficient ($\mu$, $\alpha$) as a function of coefficient of friction $\mu$ and angle $\alpha$, in accordance with one embodiment.

FIG. 16 is a graph of coef (μ, α) as a function of the coefficient of friction μ and the angle α. Two observations can be made from FIG. 8: coef (μ, α) is proportional to the coefficient of friction μ and inversely proportional to the angle α. As a result, the force T is also proportional to the coefficient of friction μ and inversely proportional to the angle α. Decreasing the angle α implies a greater force T to push back the slot member 53 out of the slot 25. The lower the angle α is, the higher the increase of the internal pressure into the tube 13 has to be in order to push the slot member 53 out of the slot 25. As a result, it is possible to set the angle α to a value preventing the rack cover 15 from being removed from the studs 22 of the rack 12.

In one embodiment, the spring 62 is enclosed in cap casing 60 in a compression state which sets a threshold pressure. For example, spring 62 has a length of 1 inch when no forces are applied to it. This spring presents a maximum load of 213.14 lb for a deflection of 37% of its length. Spring 62 is enclosed within cap casing 60 with a length deflection of 25%. This means that spring 62 presents a load of 144 lb. The internal pressure in tube 13 which can generate the same load is given by equation 8:

$$P[\text{psi}] = \text{Load [lb]} / \text{Surf [in}^2] \quad \text{(Eq. 8)}$$

where Surf is the internal surface of tube 13.

For example, if the internal surface of tube 13 is equal to 0.76 in², the internal pressure corresponding to a load of 144 lb is 189.26 psi. This internal pressure is the threshold pressure corresponding to a deflection of spring 62 equal to 25%. If the internal pressure in tube 13 is below 189.26 psi, tube 13 is hermetically closed, and if the internal pressure is superior to 189.26 psi, the internal pressure is sufficient to compress spring 62 and gas can escape from tube 13.

The following example illustrates how the internal pressure threshold can be adjusted via the pressure-adjusting bolt 63 or the lock washer 68. Table 1 presents the load of the spring 62 and the corresponding threshold pressure as a function of the displacement Dx of the pressure-adjusting bolt 63/lock washer 68 within the cap casing 60. When Dx is equal to zero, the pressure-adjusting bolt 63/lock washer 68 applies no force on the spring 62, which presents no additional deflection. In this case, the load of the spring 62 is 144 lbs, which corresponds to a threshold pressure of 189.47 psi. By screwing the pressure-adjusting bolt 63/lock washer 68, an additional compression is applied to the spring 62, which increases its load. For example, by displacing the pressure-adjusting bolt 63/lock washer 68 by 0.2 in, the total load of the spring 62 is increased up to 259.2 lb, which corresponds to a threshold pressure of 314.05 psi.

TABLE 1

| Dx [in] | Load [lb] | Pressure [psi] |
|---|---|---|
| 0.000 | 144.000 | 189.26 |
| 0.025 | 158.400 | 208.42 |
| 0.050 | 172.800 | 227.37 |
| 0.075 | 187.200 | 246.32 |
| 0.100 | 201.600 | 265.26 |
| 0.125 | 216.000 | 284.21 |
| 0.150 | 230.400 | 303.16 |
| 0.175 | 244.800 | 322.11 |
| 0.200 | 259.200 | 341.05 |

For a fixed initial compression of the spring 62, it is possible to vary the threshold pressure at which the pressure-relief valve opens and gas exhausts from the tube 13 from 189.26 to 314.05 psi by screwing the pressure-adjusting bolt 63/lock washer 68.

While the present description refers to slot members 53 to be positioned in slots 25 in order to removably and fixedly secure the rack cover 15 to the rack 12, it should be understood that any adequate fastener that allows removably securing the rack cover 15 to the rack 12 can be used. For example, bolts or screws may be used for securing the rack cover 15 to the rack 12.

Figure 17:
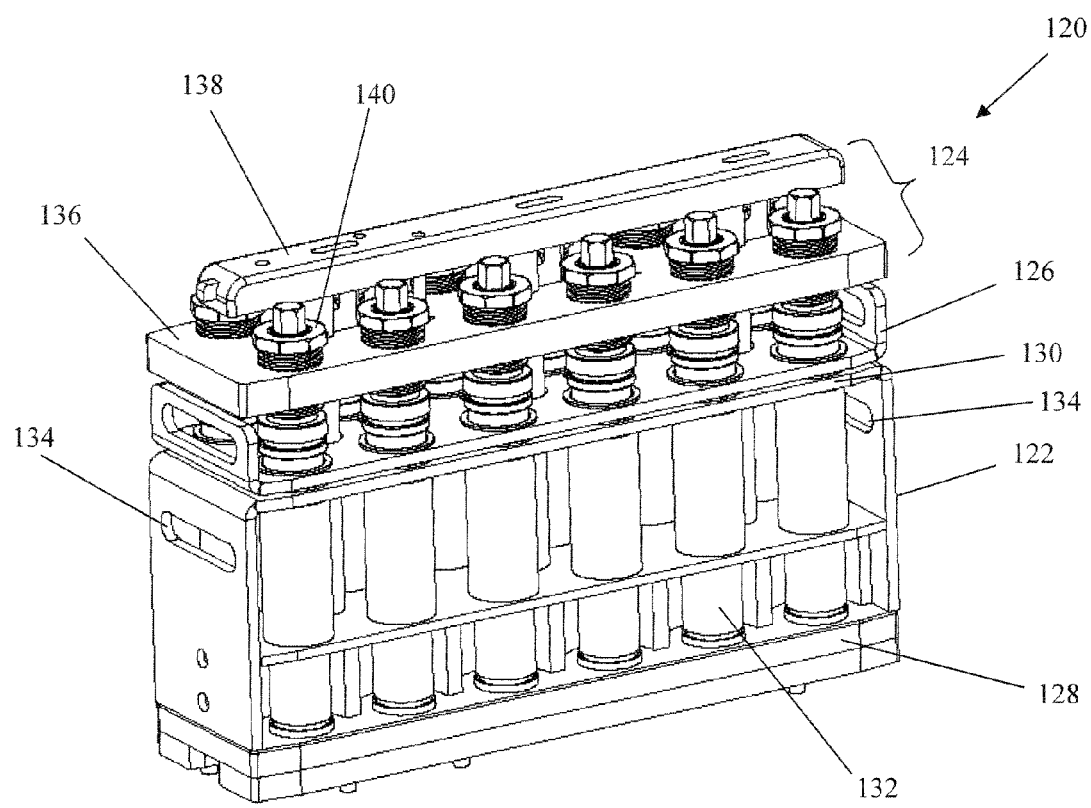
FIG. 17 is a perspective view of a rack comprising a removable transportation plate and covered by a rack cover, in accordance with an embodiment.

FIG. 17 illustrates a sample holder system 120 comprising a rack 122, a rack cover 124, and a transportation plate 126. The rack 122 comprises a base plate 128 to which a U-shaped support plate 130 is secured. The support plate 130 is provided with twelve apertures each adapted to receive a sample tube 132, and a pair of handles 134. The rack cover 124 comprises a cap-receiving plate 136 to which a clamping bar 138 is translationally secured. The cap-receiving plate 136 is provided with twelve apertures each for receiving a compression cap 140.

Figure 18:
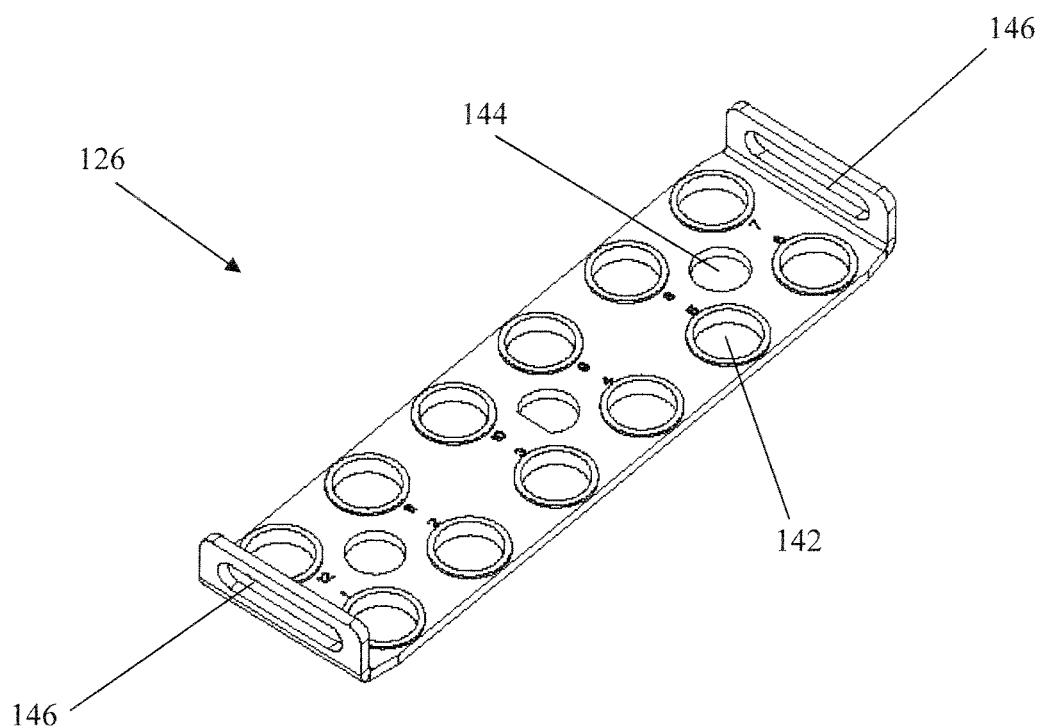
FIG. 18 is a perspective view of a transportation plate, in accordance with an embodiment.

FIG. 18 illustrates one embodiment of a U-Shaped transporting plate 126 comprising twelve tube-receiving openings 142 and three stud-receiving openings 144. The tube receiving openings 142 are each positioned to be aligned with a respective tube-receiving aperture of the support plate 130 of the rack 122, and shaped and sized to receive a tube 132. The stud-receiving openings 144 are positioned, shaped, and sized to each receive a corresponding stud of the rack 122. The transporting plate 126 is further provided with a pair of apertures 146 each forming a handle.

It should be understood that the shape, dimensions, position, and number of the tube-receiving openings 142 and the stud-receiving openings are determined in accordance with the shape, dimensions, position, and number of the tube-receiving apertures of the support plate 130 and the studs of the rack 122, respectively.

Figure 19A:
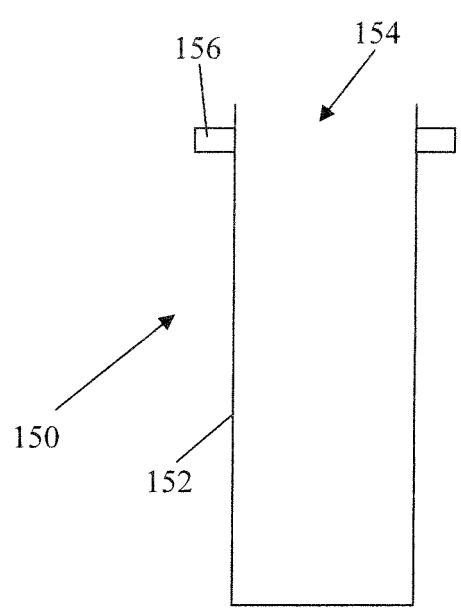
FIG. 19A is a cross-sectional view of a sample tube provided with a flange, in accordance with an embodiment.
Figure 19B:
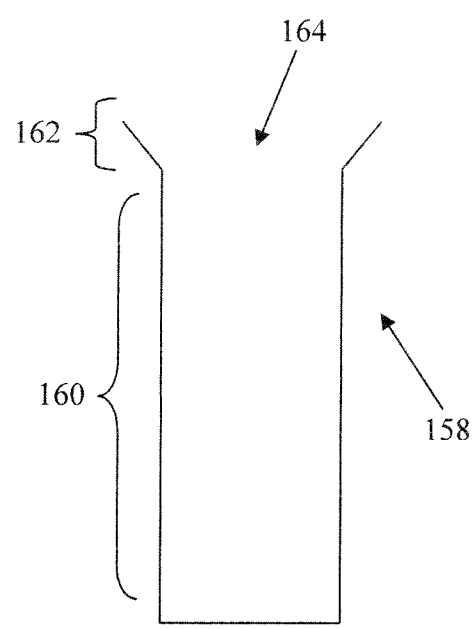
FIG. 19B is a cross-sectional view of a sample tube having a varying diameter, in accordance with an embodiment.

FIGS. 19A and 19B each provide an example of a sample tube 132 which may be used with the transporting plate 126 and the rack 122. The sample tube 150 illustrated in FIG. 19A comprises a cylindrical tube 152 having an opened end 154, and a flange circumferentially extending around the tube 152 adjacent the open end 154. It should be understood that the position of the flange 156 along the height of the tube 152 is exemplary only. For example, the flange 156 could be positioned at about half of the height of the tube 152.

The sample tube 158 illustrated in FIG. 19B is a cylindrical tube having a diameter varying along its height. The tube 158 comprises a first section 160 having a constant circumference therealong and a wide-mouthed section 162 having an increasing circumference near the opening 164 of the tube 158.

The circumference of the tube-receiving openings 142 is larger than that of the tube 150 or that of the section 160 of the tube 158 so that the tube 150 or 158 can be inserted into the opening 142. The circumference of the tube-receiving openings 142 is smaller than that of the flange 156 of the tube 150 or that of the rim of the tube 158 so that the flange 156 of the tube 150 or the wide-mouthed section 162 of the tube 158 may engage the surrounding or the rim of the aperture 142 of the transporting plate 126. As a result, the tube 150 or 158 may be supported by the transporting plate 126.

It should be understood that the shape of the sample tubes 150 and 158 is exemplary only. A sample tube to be used with the transportation plate 126 may have any adequate shape as along as at least a portion of the tube passes through the tube-receiving aperture 142 while being supported by the transporting plate 126. For example, an adequate tube can comprise two cylindrical section having different diameters.

Figure 20:
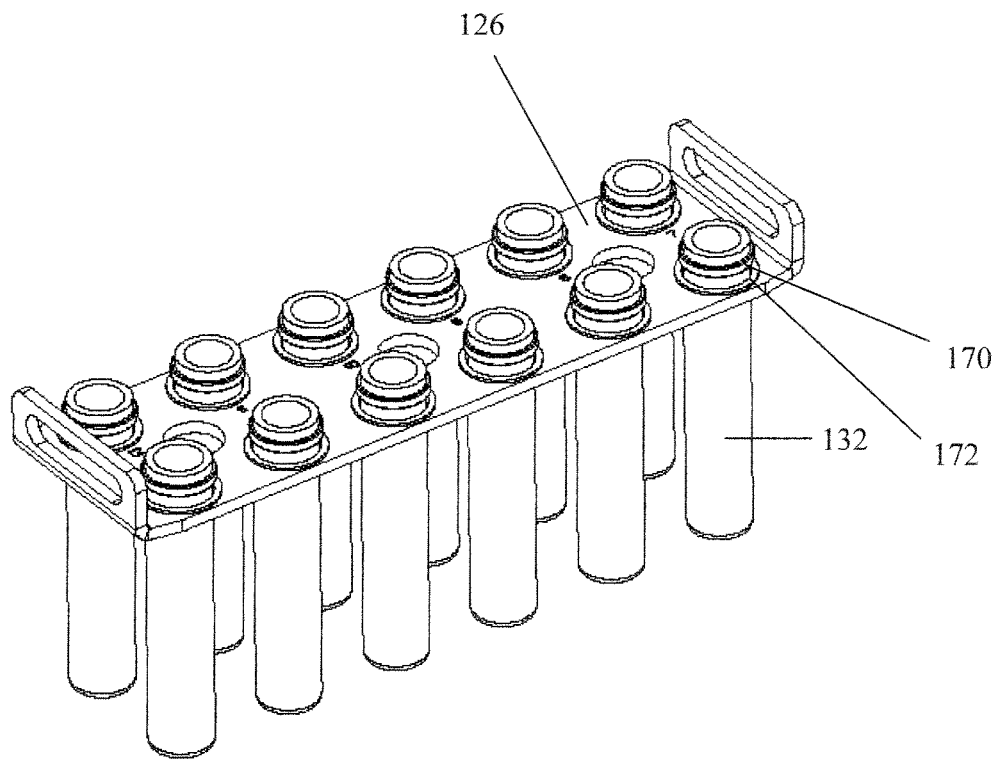
FIG. 20 is a perspective view of sample tubes when received on the transportation plate of FIG. 18, in accordance with an embodiment.

FIG. 20 illustrates the transporting plate 126 supporting twelve sample tubes 132. Each sample tube 132 is provided with a flange 170 near the opening of the tube 132. The circumference of the tube 132 is inferior to that of the opening 142 so that it can slide therein, but the circumference of the flange 170 is superior to that of the opening 142 so that the flange 170 is supported by the surrounding of the opening 142.

In one embodiment, a protective ring 172 is inserted in each tube-receiving opening 142 for protecting the rack 126 against the high temperature of the tube 132. The protective ring 172 can be made from Teflon for example.

In one embodiment, the transporting plate 126 allows the grouping of a plurality of sample tubes 132 on a same structure. The transporting plate 126 facilitates the transportation of the sample tubes 132 since a user does not have to individually transport the sample tubes 132.

Figure 21:
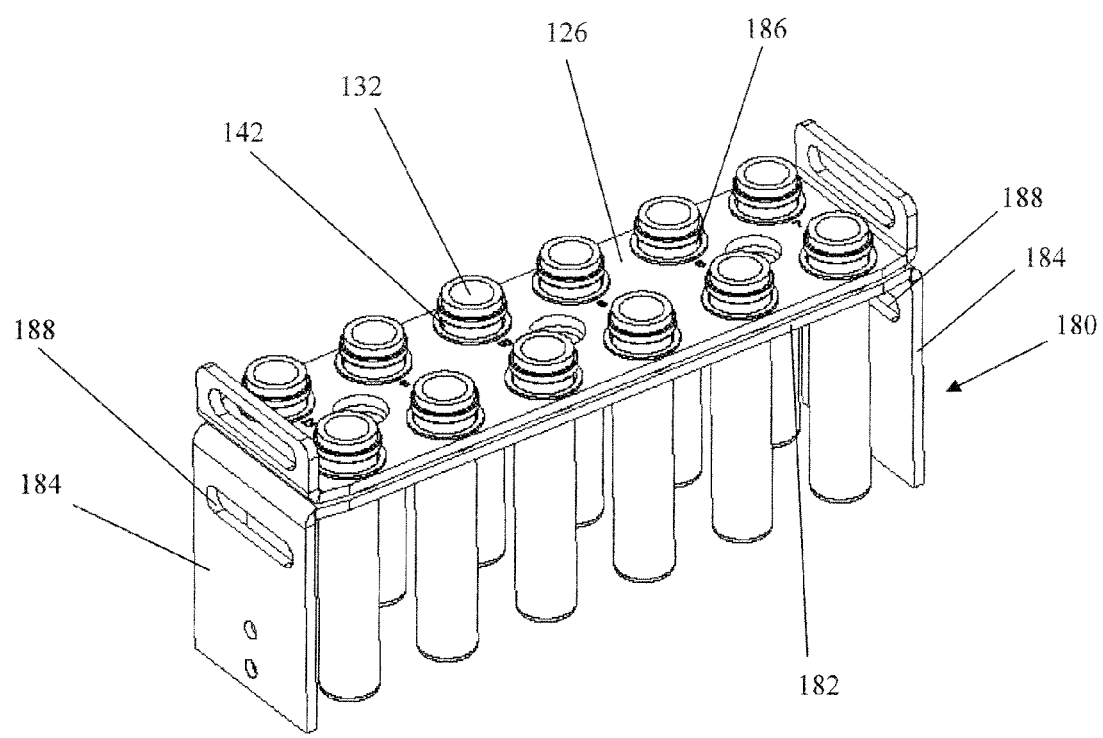
FIG. 21 is a perspective view of the transportation plate and the sample tubes of FIG. 20 when received in a holding frame, in accordance with an embodiment.

FIG. 21 illustrates a holding frame 180 for holding the transporting plate 126. The holding frame 180 comprises a top plate 182 and a pair of side plates 184, thereby providing the holding frame 180 with a U-shape. The top plate 182 comprises twelve apertures 186 each sized to receive a sample tube 132 and positioned to be aligned with a tube-receiving opening 142 of the transporting plate 126. The side plates 184 each comprise an opening 188 forming a handle. The transporting plate 126 comprising the sample tubes, as illustrated in FIG. 20, is deposited on top of the top plate 182 of the holding frame 180 so that each sample tube 132 is received in a corresponding aperture 186. Alternatively, the transporting plate 126 may be deposited on the top plate 182 and the openings 142 of the transporting plate 126 are each aligned with a respective aperture 186 of the holding frame 180. Then the sample tubes 132 are each inserted into a corresponding tube receiving opening 142, which results in the assembly illustrated in FIG. 21.

The assembly illustrated in FIG. 21 may be used in a preparation station in which a user fills the tubes 132 with a sample. Once the preparation of the samples is completed, the user may concurrently transport all of the tubes 132 by taking the handles of the transporting plate 126 and lifting the transporting plate 126. The user may then insert the tubes 132 into the rack 122. First the tubes are each aligned with a respective tube-receiving opening of the rack 122, and then the transporting plate 126 is pulled down to insert the sample tubes 132 into their respective tube-receiving opening until the transporting plate 126 engages the support plate 130 of the rack 122. Once the transporting plate 126 with the tubes 132 is deposited on the rack 122, the rack cover 124 is deposited on top of the rack 122 to obtain the sample holder system 120 illustrated in FIG. 17. The sample holder system 120 is placed into a microwave oven where the samples are heated. Once the digestion is completed, all of the tubes 132 may be concurrently brought to an analysis station where the user may analyse the digested or extracted samples.

Figure 22:
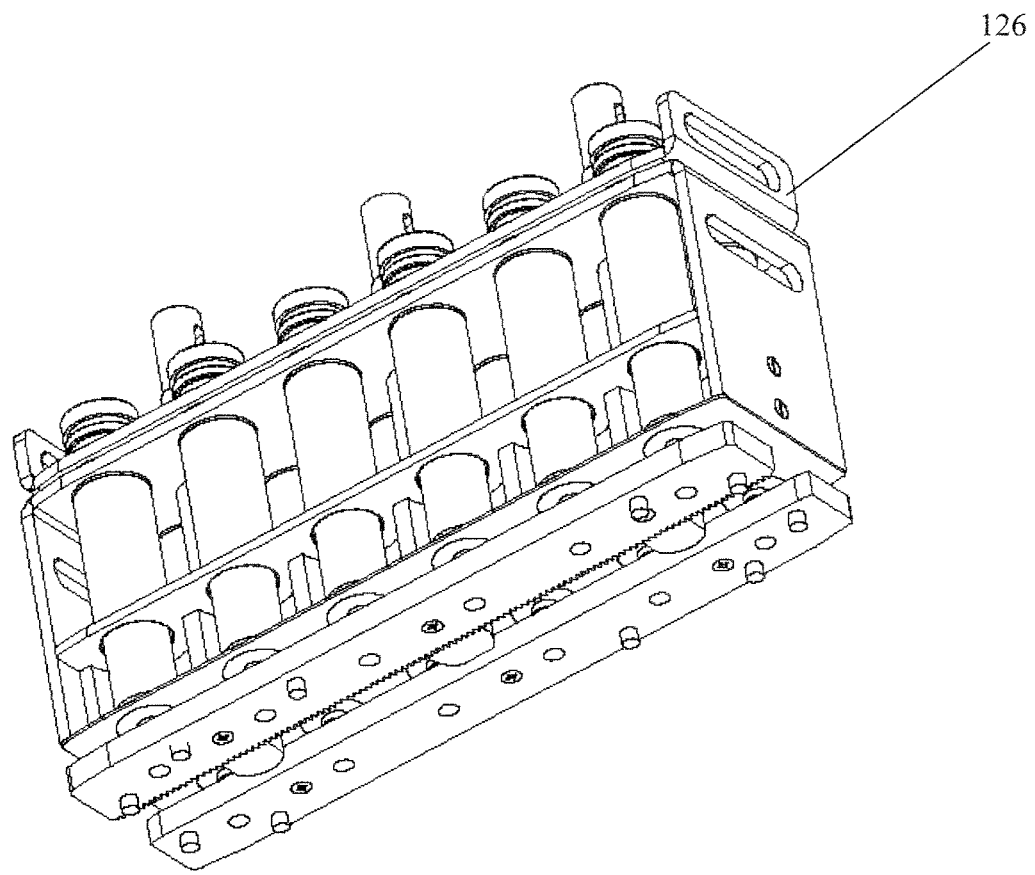
FIG. 22 is a perspective bottom view of the rack of FIG. 17, in accordance with an embodiment.

While in FIG. 22 the handles of the support plate 126 are upwardly directed and engage the support plate 130 of the rack 122, it should be understood that the tubes 132 may be inserted in the transporting plate 126 so that the handles of the supporting plate 126 are downwardly directed.

It should be understood that the shape of the holding frame 180 is exemplary only as along as it allows the transporting plate 126 to be supported. For example, the holding frame may comprise a top plate having tube-receiving apertures and four legs to have a table-like shape.

In one embodiment, the tube-receiving openings 142 of the transporting plate 126 and/or the tube-receiving apertures of the support plate 130 may be identified by an identifier such as a number for example. For example, a number comprised between one and twelve may be printed or engraved adjacent to the corresponding tube-receiving opening 142 of the transporting plate 126 and/or the tube-receiving aperture of the support plate 130. In another embodiment, only one tube-receiving opening 142 of the transporting plate 126 and/or the first tube-receiving aperture of the support plate 130 is identified as being the first opening.

It should be understood that the shape of the transportation plate 126 is exemplary only as long as it allows at least one sample tube to be supported by a sample structure. For example, the transportation plate may be a rectangular and planar plate provided with twelve apertures, or it may be provided with a single aperture. In one embodiment, twelve individual transportation plates each holding a single tube are inserted into the receiving apertures of the holding frame 180.

It should be understood that the rack cover 15 or 70 may be used in the sample holder system 120. Similarly, the rack 122 may correspond to the rack 12 provided with studs 22 having an adequate height.

Figure 23:
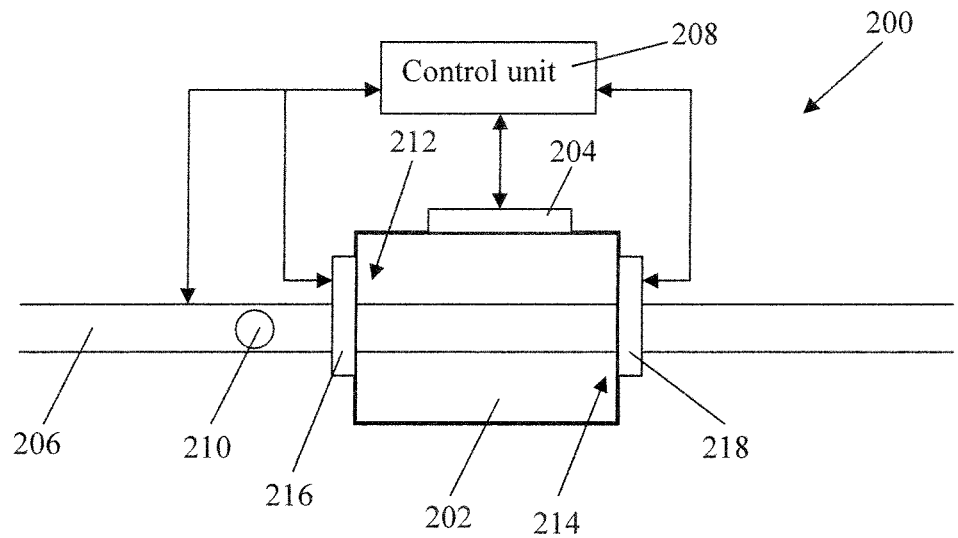
FIG. 23 is a block diagram of an automated digestion system comprising a straight conveyor extending through a microwave oven, in accordance with an embodiment.

FIG. 23 illustrates one embodiment of an automated microwave oven 200 for heating a sample to be extracted or decomposed. The oven 200 comprises a heating chamber 202, a microwave generator 204, a conveyor 206, and a control unit 208. The heating chamber 202 is adapted to receive a sample holder 210 containing the sample to be heated. The microwave generator 204 is adapted to generate microwaves and operatively connected to the heating chamber 202 in order to propagate the generated microwave energy into the heating chamber 202. For example, the microwave generator 204 may be positioned in the heating chamber 202. In another embodiment, the microwave generator 204 is separate from the heating chamber 202 and a microwave waveguide connects the microwave generator 204 to the heating chamber 202 in order to transport and propagate the generated microwaves into the heating chamber 102.

The conveyor 206 is adapted to receive and transport the sample holder 210 through the heating chamber 202 which is provided with an entrance opening 212 and an exit opening 214. An entrance door 216 and an exit door 218 are provided for closing the entrance opening 212 and the exit opening 214, respectively. The entrance and exit door 216 and 218 are made from a microwave-resistant material in order to prevent the microwaves from propagating outside the heating chamber 202. The conveyor 206 extends through the heating chamber 202 via the entrance and exit openings 212 and 214. It should be understood that the generation of microwaves is stopped when the sample holder 210 enters or exits the heating chamber 202.

The control unit 208 is configured for controlling the conveyor 206, the microwave generator 204, and the entrance and exit doors 216 and 218. The control unit 208 may be adapted to adjust the power or the duty cycle of the microwaves generated by the microwave generator 204 and/or the duration of the microwave generation in order to heat the sample contained in the sample holder 210. The control unit 208 is further adapted to control the displacement of the conveyor 206 in order to control the speed of displacement and position of the sample holder 210. The control unit 208 is also adapted to coordinate the opening and closing of the doors 216 and 218 with the entry and exit of the sample holder 210 from the heating chamber 210.

In one embodiment, the microwave generator 204 is adapted to control the power of the generated microwaves. In this case, the control unit may adjust the power of the generated microwaves to a desired value comprised between 0% and 100% of the maximum power of the microwave generator 204. The microwave generator 20 is then operated continuously during a predetermined period of time at a desired power to heat the sample at a desired temperature.

In another embodiment, the power of the microwave generator 204 is not controllable which means that only the maximum microwave power may be delivered by the microwave generator 204. In this case, the microwave generator 204 operates according to a duty cycle.

In one embodiment, the doors 216 and 218 are each provided with a microwave quarter-wave trap for preventing any leakage of microwaves outside of the heating chamber. The oven may also be provided with microwave sensor for detecting any leakage of microwaves outside of the heating chamber 202. In this case, the control unit 208 may be adapted to stop the microwave generator 204 upon detection of a microwave leakage.

In one embodiment, the control unit 208 comprises a processor, a memory, and a command input device. A user enters parameters such an identification of the sample, a desired temperature, a desired microwave power, a heating time, and/or the like, into the control unit 208 via the command input device.

In one embodiment in which the user enters a desired temperature for the sample, the microprocessor is adapted to determine the microwave power or the duty cycle corresponding to the desired temperature for the sample. For example, the memory may be provided with a database of temperatures and corresponding microwave powers, or a database of desired temperatures and corresponding duty cycles. The processor may also be adapted to determine the microwave power or duty cycle in accordance with the type of sample contained in the sample holder 210 and/or the type of the sample tube.

It should be understood that any adequate conveyor system compatible with microwaves may be used. For example, the conveyor 206 may be a belt conveyor, a chain conveyor, a lineshaft roller conveyor, or the like.

In one embodiment, the sample holder 210 is provided with rolling elements rotatably secured therebelow. The conveyor 206 may comprise a planar surface extending through the heating chamber 202, on which the sample holder 210 may roll, and a driving device adapted to roll the sample holder 210 on the planar surface. Any adequate driving mechanism may be used.

It should be understood that any adequate sample holder 210 adapted to microwave heating may be used. For example, the sample holder may be made from glass or Teflon. The sample holder may be adapted to receive a single sample or a plurality of samples. For example, the sample holder 10 or 120 may be used.

The heating chamber 202 may have any adequate shape and size for receiving the sample holder 210 and can be made from any adequate type of microwave-resistant material so that generated microwaves do not exit the heating chamber 202.

In one embodiment, the conveyor 206 and the control unit 208 are adapted to stepwise transport the sample holder 210. In this case, the sample holder 210 occupies a series of predetermined positions during a corresponding predetermined period of time. In another embodiment, the conveyor 206 and the control unit 208 are adapted to continuously move the sample holder 210 within the oven 200.

While the present description refers to a single heating chamber 202, it should be understood that the oven 200 may comprise more than one heating chamber each crossed by the conveyor 206 and each provided with movable doors and a microwave generator. The heating chambers may be physically secured together so that the sample holder 210 enters a second heating chamber while exiting a first heating chamber. Alternatively, the heating chambers may be physically spaced apart.

Figure 24:
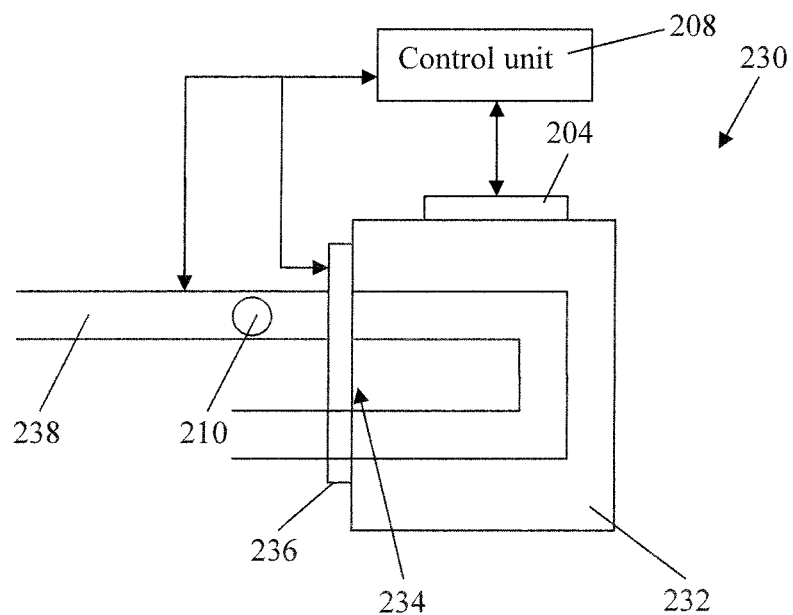
FIG. 24 is a block diagram of an automated digestion system comprising a U-shaped conveyor extending through a microwave oven, in accordance with an embodiment.

FIG. 24 illustrates one embodiment of an automated microwave 230 comprising a heating chamber 232 having a single opening 234 which is used for both entering and exiting the sample holder 210 and closed by a single door. In this embodiment, the conveyor 238 may be U-shaped.

Figure 25:
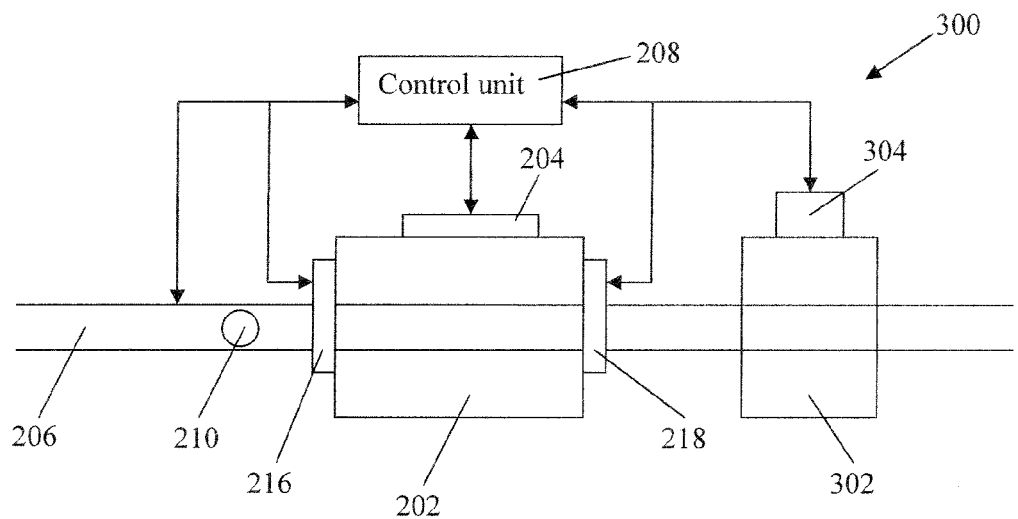
FIG. 25 is a block diagram of an automated digestion system extending through a microwave oven and a cooling chamber, in accordance with an embodiment.

FIG. 25 illustrates one embodiment of a microwave oven 300 provided with the same elements as the oven 200 and further comprising a cooling chamber 302. The cooling chamber 302 is adapted to receive the sample holder 210 and the conveyor 206 extends through the cooling chamber 202. The cooling chamber 302 is positioned adjacent to the heating chamber 302 so that the sample holder 210 may be brought into the cooling chamber 302 after leaving the heating chamber 202. The cooling chamber 302 is provided with a cooling unit 304 adapted to cool the sample contained into the sample holder 210. Any adequate cooling unit may be used. For example, the cooling unit may be a refrigerating unit. In another example, the cooling unit may comprise at least one fan positioned to blow air on the sample holder 210 or draw air outside of the cooling chamber 302 in order to remove heat from the sample holder 210 and cool the sample.

Figure 26:
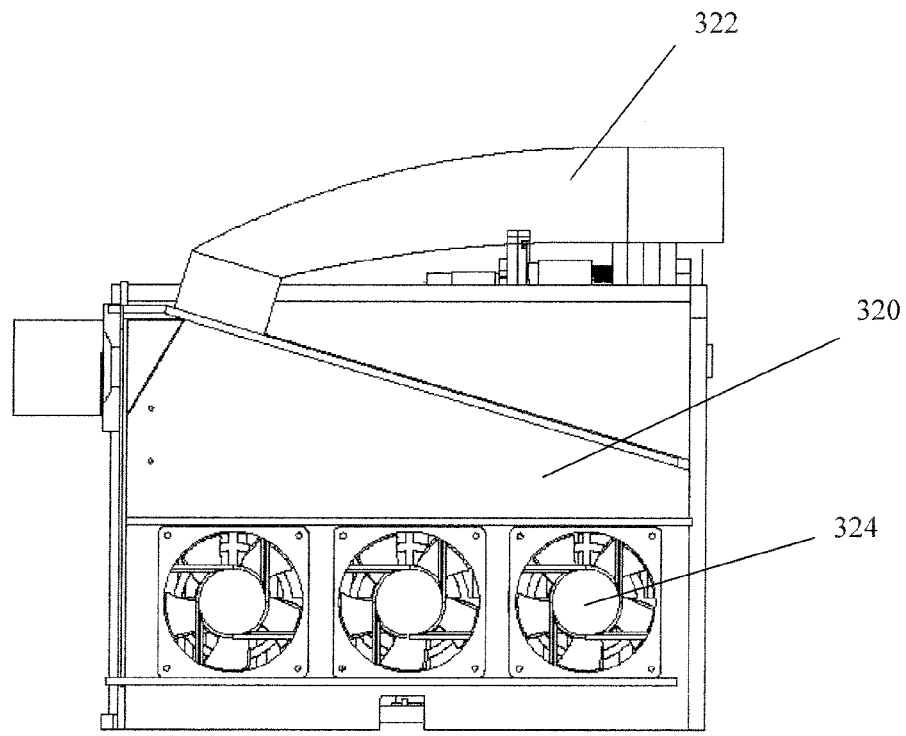
FIG. 26 is a cross-sectional side view of a cooling chamber, in accordance with an embodiment.

FIG. 26 illustrates one embodiment of a cooling chamber 320 provided with three fans in order to cool the sample holder 210. An air outlet 322 positioned near the top of the cooling chamber 320 and connected to the outside of the oven 300 allows heated air to exit the cooling chamber 320. Three fans 324 are located near the bottom of the cooling chamber 320 and adapted to draw air contained in the cooling chamber 320 outside thereof. When the fans 324 are operated, air contained in the cooling chamber 320 is expulsed outside and fresh air is drawn from the outside into the cooling chamber 320, thereby creating an air current which cools down the sample holder.

In one embodiment, the user enters cooling parameters such a cooling duration, a cooling unit power, a desired end cooling process temperature, and/or the like in the control unit 208 which controls the cooling process in accordance with the cooling parameters.

In one embodiment, the oven 300 is free from any cooling chamber 202 and the cooling device 304 such as a fan is located at the exit of the heating chamber 202.

Figure 27:
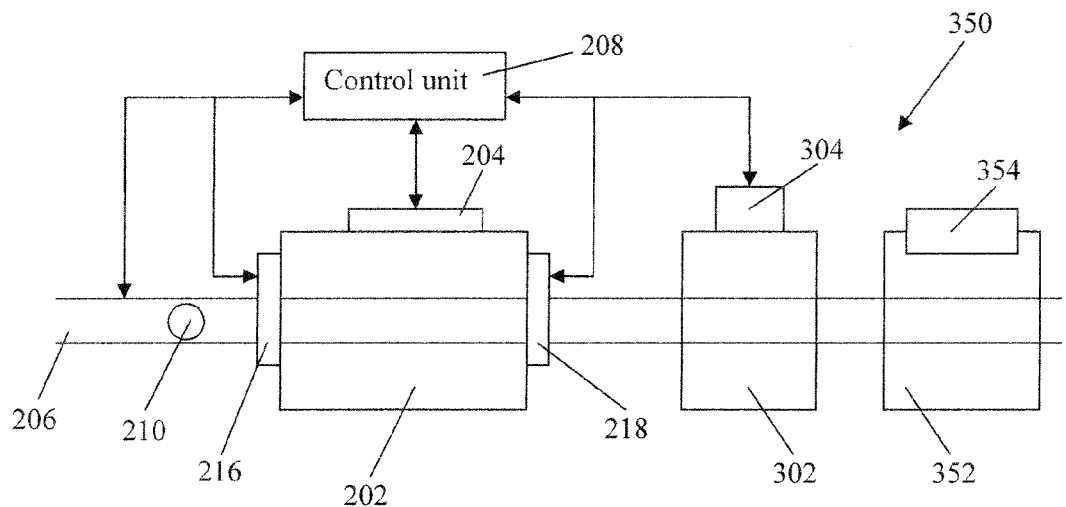
FIG. 27 is a block diagram of an automated digestion system comprising a straight conveyor extending through a microwave oven, a cooling chamber, and an auto-venting chamber, in accordance with an embodiment.

FIG. 27 illustrates one embodiment of a microwave oven 350 comprising all of the elements of the oven 300 and further comprising a venting chamber 352 provided with an unsealing unit 354. When the sample holder 210 is provided with a lid or cap for hermetically enclosing the sample into the sample holder 210, the unsealing unit 354 is adapted to unseal the sample holder 210 so that pressurized gas contained in the sample holder 210 may exit the sample holder 210. The control unit 208 is further adapted to control the unsealing unit 354. It should be understood that any adequate cap for hermetically sealing the sample holder 210 and any adequate unsealing device adapted to unseal the sample holder 210 may be used.

In one embodiment, the sample holder 210 is provided with a thread so that a lid may be screwed therein. The lid is screwed in the sample holder 210 to hermetically close the sample holder 210 so that no gas may exit the sample holder 210 during the heating process. In this case, the unsealing unit may comprise an automated arm provided with any adequate mechanisms for unscrewing the lid such as pincers, a suction cup, or the like.

Figure 28:
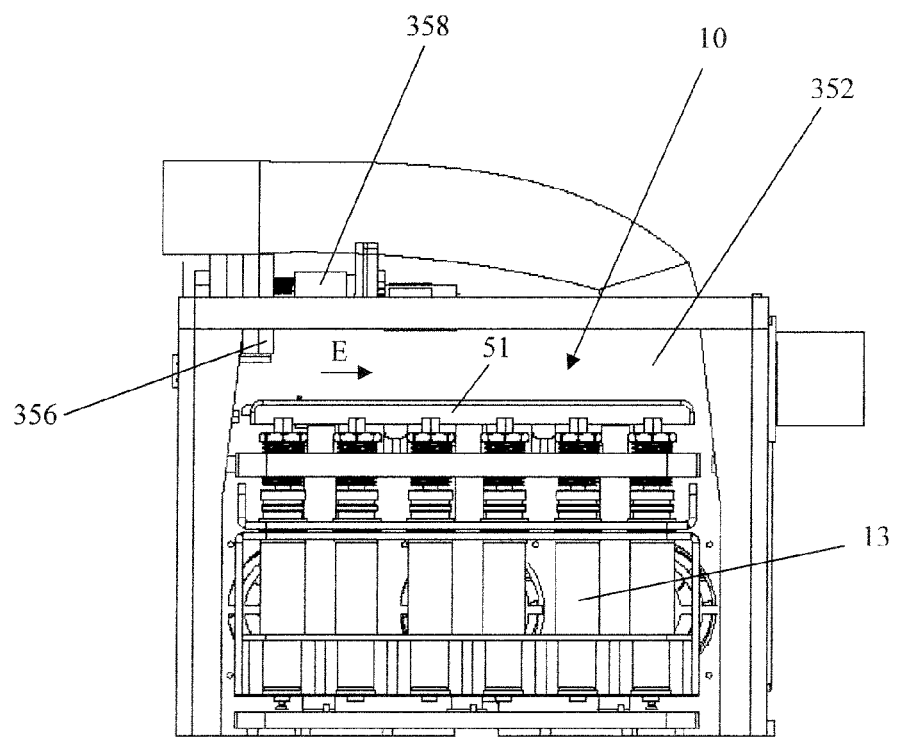
FIG. 28 is a cross-sectional side view of an auto-venting chamber, in accordance with an embodiment.

In another embodiment, the sample holder may be the sample holder system 10 and the unsealing device comprises a moving arm adapted to push on the front portion of the clamping bar 51 in order to at least partially dislodge the slot members 53 from the slots 25, as illustrated in FIG. 28. The venting chamber 352 is provided with a movable arm 356 of which the displacement is controlled by a motor 358. By actuating the motor 358, the movable arm 356 is moved towards the clamping bar 51 of the sample holder system 10 as illustrated in FIG. 28 (arrow E). The movable arm 356 then engages and pushes the clamping bar 51, thereby dislodging the slot members 53 from the slots 25 and unsealing the tubes 13.

In a further embodiment, the unsealing device may comprise a movable arm provided with pincers for pulling the rear end of the clamping bar 51.

In a further embodiment, the sample holder may comprise a clamping bar having a safety mechanism such as the clamping bar 72 illustrated in FIG. 8. The unsealing device may comprise at least one moving arm adapted to downwardly push on the locking member 84 to disengage the locking member 84 from the stud 22 and horizontally push on the clamping bar 72 to dislodge the slot members from the stud slots. In one embodiment, the moving arm is beveled in order to concurrently engage the locking member 84 and the clamping bar 72 and exert a downward force of the locking member 84 and a substantially horizontal force on the clamping bar 72.

In one embodiment, the venting process requires a precise positioning of the sample holder 210 with respect to the unsealing device 354. In this case, position sensors such as mechanical position sensors or optical position sensors may be used by the control unit 208 to determine whether the position of the sample holder 210 within the venting chamber 352 is adequate. If the control unit 208 determines that the position of the sample holder 210 is inadequate, a sample holder positioning device controlled by the control unit 208 is used for moving the sample holder to an adequate position within the venting chamber 352. It should be understood that any adequate mechanical positioning device adapted to move the sample holder to a desired position within the venting chamber 352 may be used.

In another embodiment, no precise positioning of the sample holder 210 with respect to the unsealing device 354 is required.

In one embodiment, the venting chamber 352 is fluidly connected to a cooling chamber provided with at least one fan adapted to draw air out of the cooling chamber. In this case, gases leaking out of the sample holder during the venting process are drawn out of the venting and cooling chambers by the fan.

In one embodiment, the heating chamber 202 and/or the cooling chamber 302 and/or the venting chamber 352 is(are) provided with a temperature sensor for measuring the temperature of the sample holder 210 and/or the sample contained in the sample holder 210. In this case, the control unit 208 is adapted to control the microwave generator 204, the cooling unit 304, and/or the unsealing unit 354 in accordance with the temperature of the sample holder 210 and/or the sample in the respective chamber 202, 302, 352. For example, if a temperature sensor is present in the heating chamber 202, or is positioned in such a way or such a location to read a sample temperature in tube 132, the control unit 208 can adjust the power and/or the duty cycle and/or the heating time of the generated microwaves in accordance with the sensed temperature to heat the sample up to a desired temperature. In another example in which the cooling chamber 302 is provided with a temperature sensor, the sample holder 210 may only exit the cooling chamber 302 when the temperature of the sample and/or the sample holder 210 has decreased below a predetermined temperature. The control unit 208 may also control the cooling unit 304 in accordance with the sensed temperature. In a further example in which the venting chamber 352 is provided with a temperature sensor, the unsealing unit 354 is activated by the control unit 208 only when the temperature of the sample holder 210 and/or the sample within the venting chamber 352 has decreased below a predetermined venting temperature.

In one embodiment, several sample holders 210 are positioned on the conveyor and are automatically brought to the heating chamber 202, the cooling chamber (if any), and the venting chamber (if any) by the conveyor 206. The control unit 208 may apply same parameters for heating, cooling, and/or venting all of the sample holders 210. Alternatively, the control unit 208 is adapted to apply different parameters for each sample holder 210. For example, a first set of parameters may be applied to the first sample holder, a second set of parameters may be applied to the second sample holder, etc.

In one embodiment, each sample holder 210 is provided with an identification (ID) device and the oven 200, 300, 350 is provided with an ID reader adapted to read the ID device. For example, the sample holder 210 can be provided with a bar code and the oven 200, 300, 350 can comprise a bar code reader. The user enters the bar code ID for each sample holder 210 and the corresponding heating and/or cooling and/or venting parameters into the control unit 208 before starting the heating process. When a sample holder 210 enters the heating chamber 202 or before entering in the heating chamber 202, the bar code reader reads the ID of the sample holder 210 which is transmitted to the control unit 208. The control unit 208 retrieves the heating parameters corresponding to the ID and controls the microwave generator 204 in accordance with the heating parameters. The control unit 208 also retrieves the cooling and/or venting parameters from the memory and controls the cooling and/or venting processes in accordance with the retrieved cooling and/or venting parameters. In one embodiment, the bar code may comprise bars inked on the sample holder. In another embodiment, the bar code may comprise slots made into the sample holder. In a further embodiment, at least one magnet is used for identifying each sample holder 210 and the ID reader is a magnetic reader. Alternatively, magnets are used to represent binary numbers, and more than one magnet is used.

In another embodiment, the control unit 208 is provided with a clock which is used for identifying the sample holders 210. The control unit can identify the different sample holders 210 using the heating times and the time required for transporting the sample holders 210 from one position to another in the oven 200, 300, 350.

Figure 30:
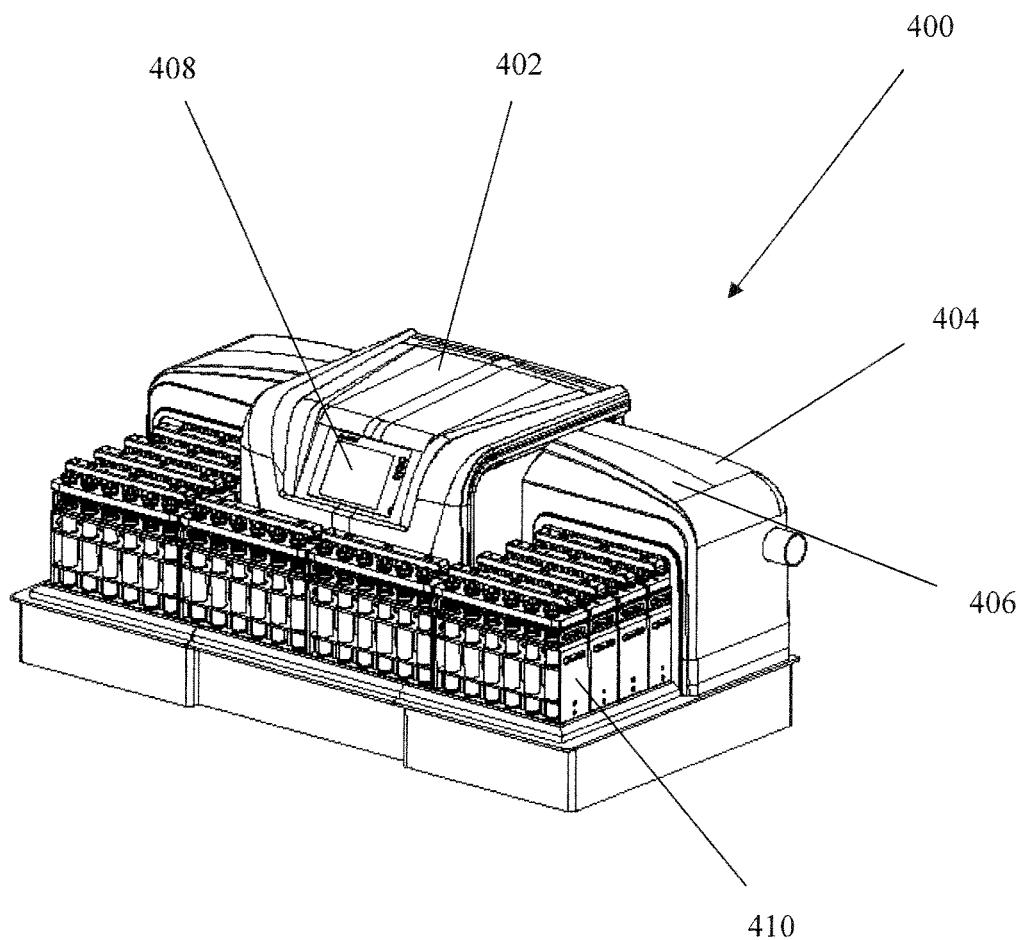
FIG. 30 is a photograph of an automated digestion apparatus, in accordance with an embodiment.

In one embodiment, the microwave oven 200, 300, 350 is sized and shaped to be portable. For example, in one embodiment, the entire system, including the heating chamber, the cooling chamber, and the venting chamber as illustrated in FIG. 30, is 26 inches in height×26 inches in width×23.5 inches in depth. The heating chamber is 21 inches in width× 13 inches in height×4.5 inches in depth. The cooling and venting areas are each 20 inches in width×19 inches in height×13.5 inches in depth. In one embodiment, the rack is 14.7 inches in length×4 inches in width and can have varying heights, such as 10 inches, 12.5 inches, etc. These dimensions are exemplary only and should not be construed as limiting.

Figure 29:
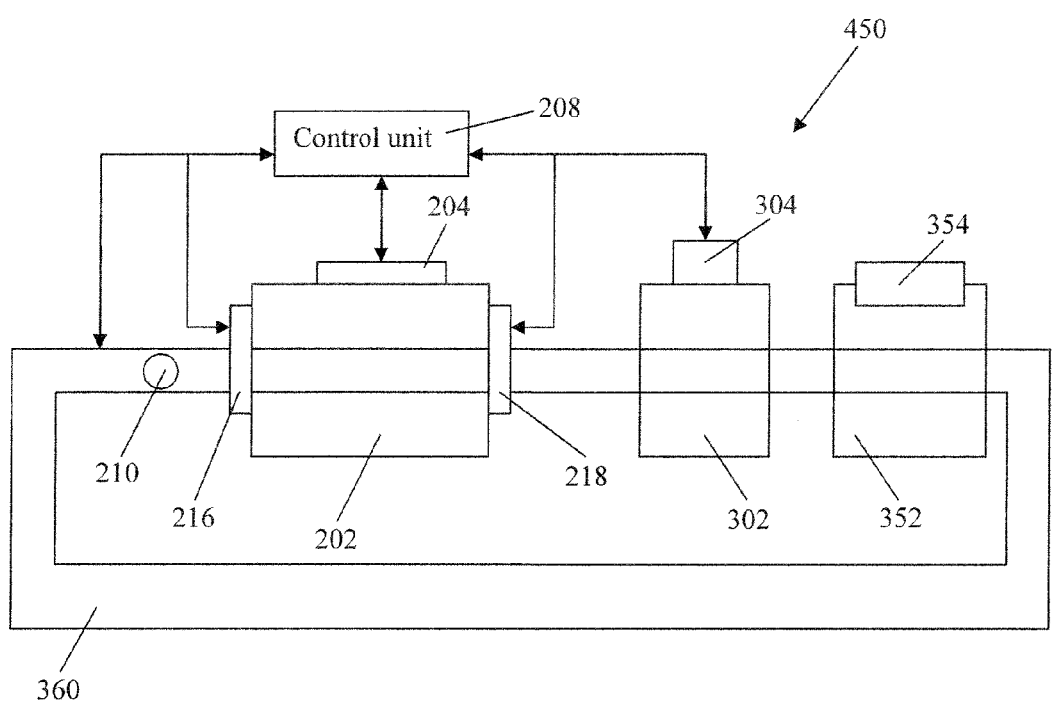
FIG. 29 is a block diagram of an automated digestion system comprising a conveyor extending through a microwave oven, a cooling chamber, and an auto-venting venting chamber, in accordance with an embodiment.

FIG. 29 illustrates one embodiment of a microwave oven 450 comprising all of the elements of the oven 400 but having a closed-loop conveyor 360. The oven 450 may be used for heating a plurality of sample holders without any surveillance from a technician, over night for example. A same sample holder may pass through the heating chamber 202, the cooling chamber 302 (if any), and the venting chamber 352 (if any) several times to be heated, cooled, and/or vented several times.

In one embodiment, each sample holder 210 is provided with an ID and the oven 450 is provided with at least one ID reader. The user enters the heating and/or cooling and/or venting parameters for each ID into the control unit 208 of the oven 450. When a sample holder enters the heating chamber 202 and/or the cooling chamber 302 and/or the venting chamber 352, the control unit 208 identifies the sample holder 210 using the ID and applies the corresponding parameters retrieved from the memory. In one embodiment, the control unit 208 is adapted to count the number of sample holders 210 and stop the conveyor 360 when the last sample holder 210 has completed the heating/cooling/venting cycle. In another embodiment, the control unit 208 is adapted to store the ID of the first sample holder entering the heating chamber 202 in order to identify it as being the number one sample holder and to stop the conveyor when the number one sample holder is about to enter the heating chamber for a second time. Alternatively, the control unit 208 is adapted to determine when the last rack of a series of pre-programmed racks exits the heating chamber 202 or the cooling chamber 302 or the venting chamber 352.

While in the present description, the heating chamber 202 of the ovens 200, 300, 400, and 450 is provided with an entrance and an exit doors for preventing the microwaves from propagating outside of the heating chamber 202, it should be understood that the heating chamber may comprise a single door from allowing the entrance and exit of the sample holder 210. In this case, the conveyor may be shaped to form a U-turn inside the heating chamber 202.

While FIGS. 25, 27, and 29 illustrate a microwave oven in which the heating chamber 202, the cooling chamber 302, and/or the venting chamber 352 are physically spaced apart, it should be understood that the chambers 202, 302, and 352 may be physically regrouped to form a tunnel. The microwave generator 204, the cooling unit 304, and the unsealing unit 354 are positioned along the tunnel at different positions. At least two microwave-barrier doors are positioned on each side of the heating chamber 202 to define a heating station within the tunnel.

FIG. 30 illustrates an automated digestion system 400 comprising a microwave oven 402, a cooling station 404, a venting station 406, a control unit 408, and a conveyor (not shown). The automated digestion system 400 is adapted to receive fourteen sample holders 410 such as sample holder systems 10 or 120, and successively heat, cool, and vent them. As each sample holder 410 comprises twelve sample tubes, up to one hundred sixty eight samples may be digested in an automated fashion by the automated digestion system 400, thereby provided an automated digestion system having an improved throughput.

In one embodiment, the microwave oven 402 is removable from the automated digestion system 400 and may be used in a non-automated fashion. In this case, the user of the oven 402 manually inserts and removes the sample holder 410.

In one embodiment, the control unit 408 applies the same heating and/or cooling and/or venting parameters to all of the sample holders 410. In another embodiment, the user may enter different operating parameters for each sample holder 410.

Figure 31:
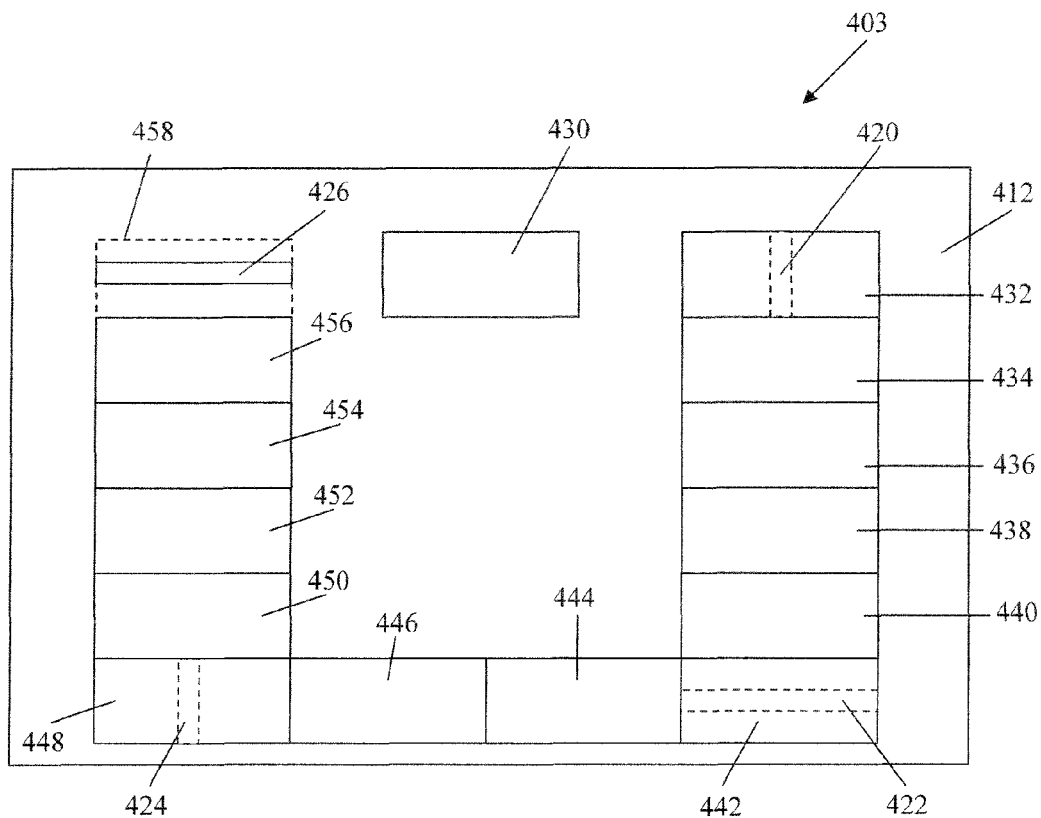
FIG. 31 is a block diagram illustrating a first disposition of sample holders on a conveyor, in accordance with an embodiment.

FIG. 31 illustrates one embodiment of a conveyor 403 which may be part of the automated digestion system 400. The conveyor 403 comprises a planar plate 412 on which sample holders 430-456 are deposited. Low friction feet or balls are rotatably secured below each sample holder 430-454 so that the sample holder 430-456 may roll or slide on the planar plate 412. The planar plate 412 is sized to receive fifteen sample holders. However, only fourteen sample 430-456 holders are placed on the planar plate 412 so that an available position 458 is free from any sample holder. The planar plate 412 is provided with four rectangular openings under which a corresponding conveyor belt 420-426 is positioned.

Figure 32:
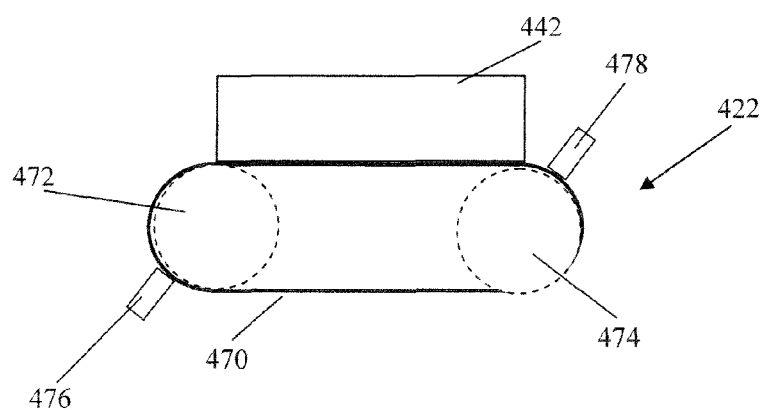
FIG. 32 is a side view of a conveyor belt, in accordance with an embodiment.

FIG. 32 illustrates one embodiment of the conveyor belt 422 which comprises a closed loop belt 470, two driving wheels 472 and 474, and two rack engaging members 476 and 478. The wheels 472 and 474 are driven by at least one motor controlled by the control unit of the automated digestion system. When the wheels 472 and 474 are anti-clockwise rotated, the rack engaging member 478 is moved towards the sample holder 442, abuts against the rear portion of the sample holder 442, and exerts a force on the sample holder 442 which rolls to the next position.

Figure 33:
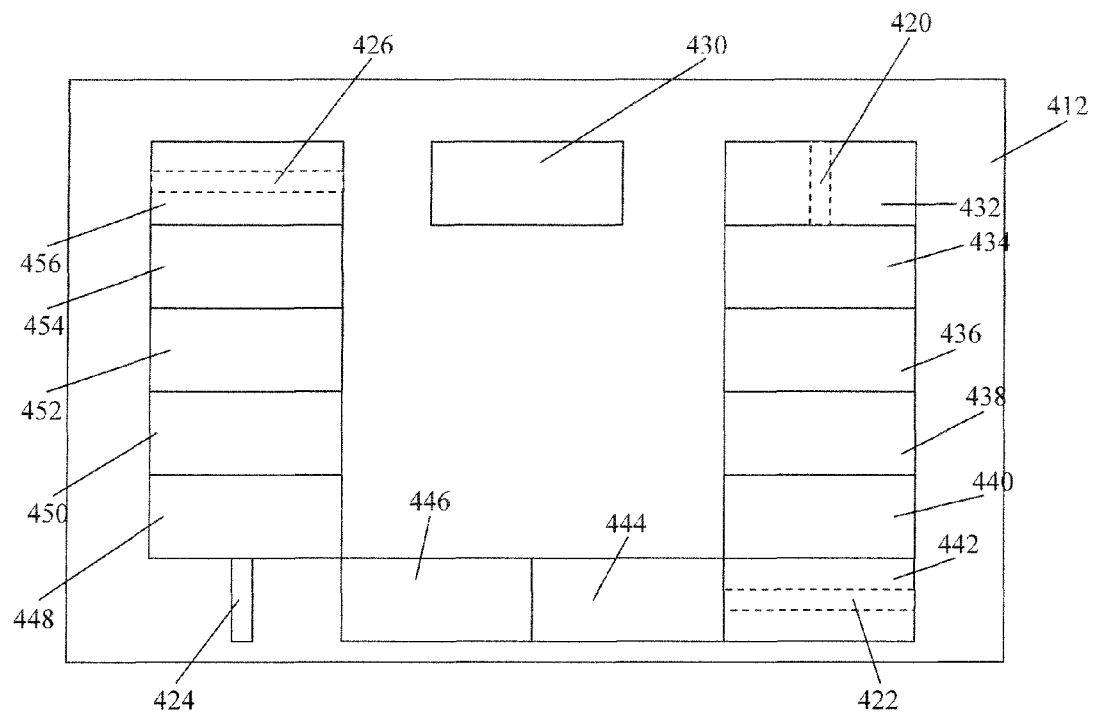
FIG. 33 is a block diagram illustrating a second disposition of sample holders on the conveyor of FIG. 31, in accordance with an embodiment.
Figure 34:
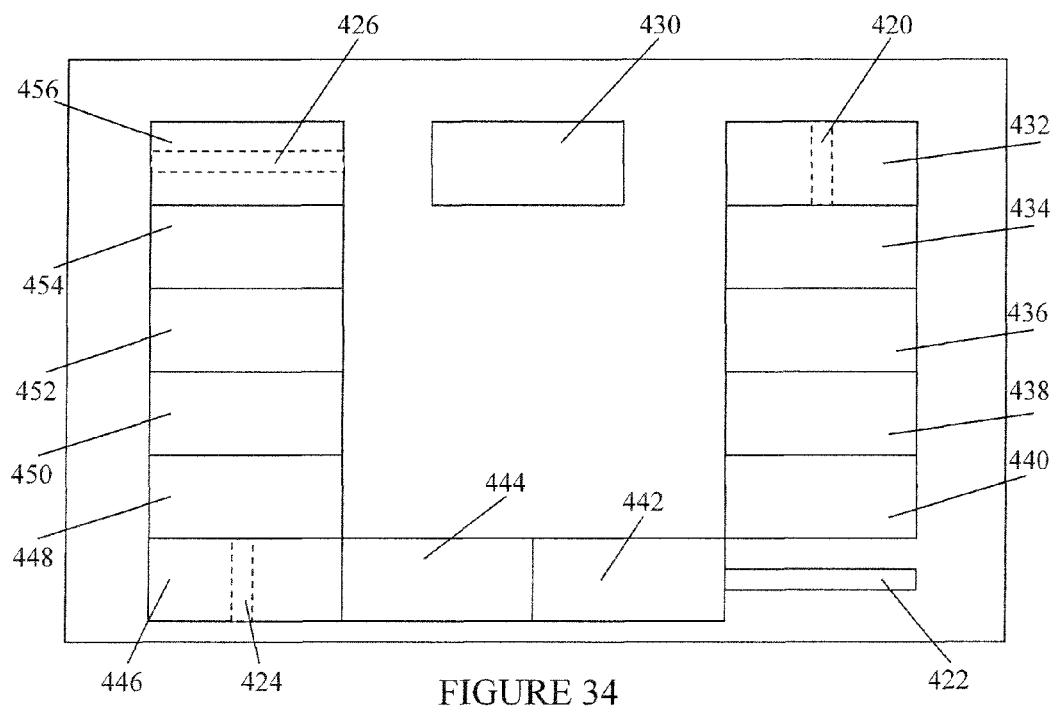
FIG. 34 is a block diagram illustrating a third disposition of sample holders on the conveyor of FIG. 31, in accordance with an embodiment.
Figure 35:
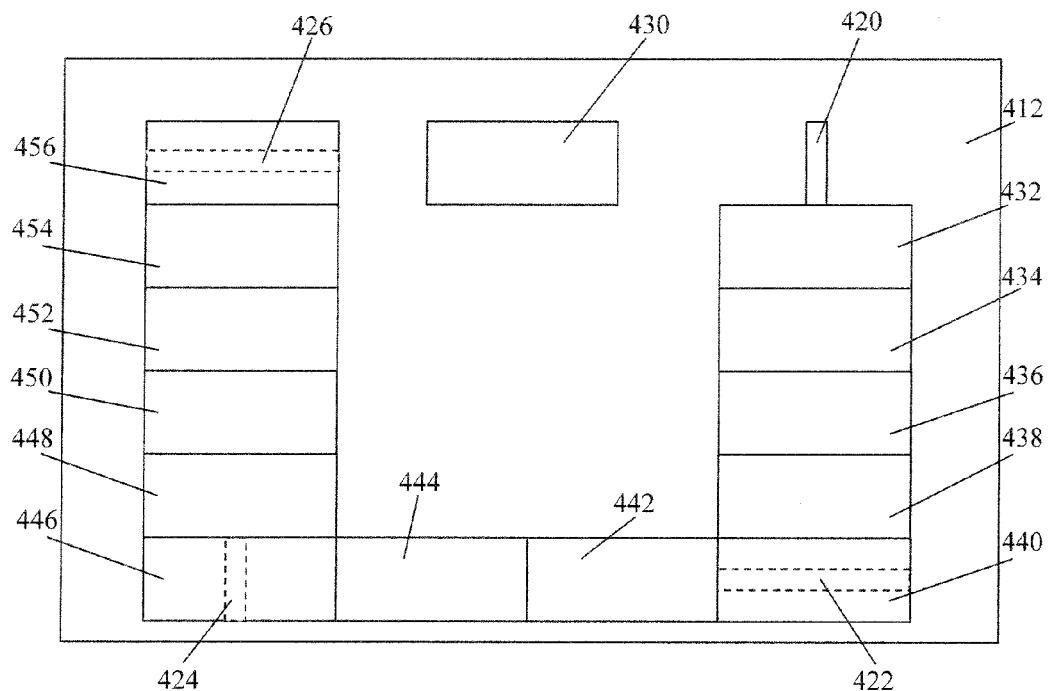
FIG. 35 is a block diagram illustrating a fourth disposition of sample holders on a conveyor, in accordance with an embodiment.
Figure 36:
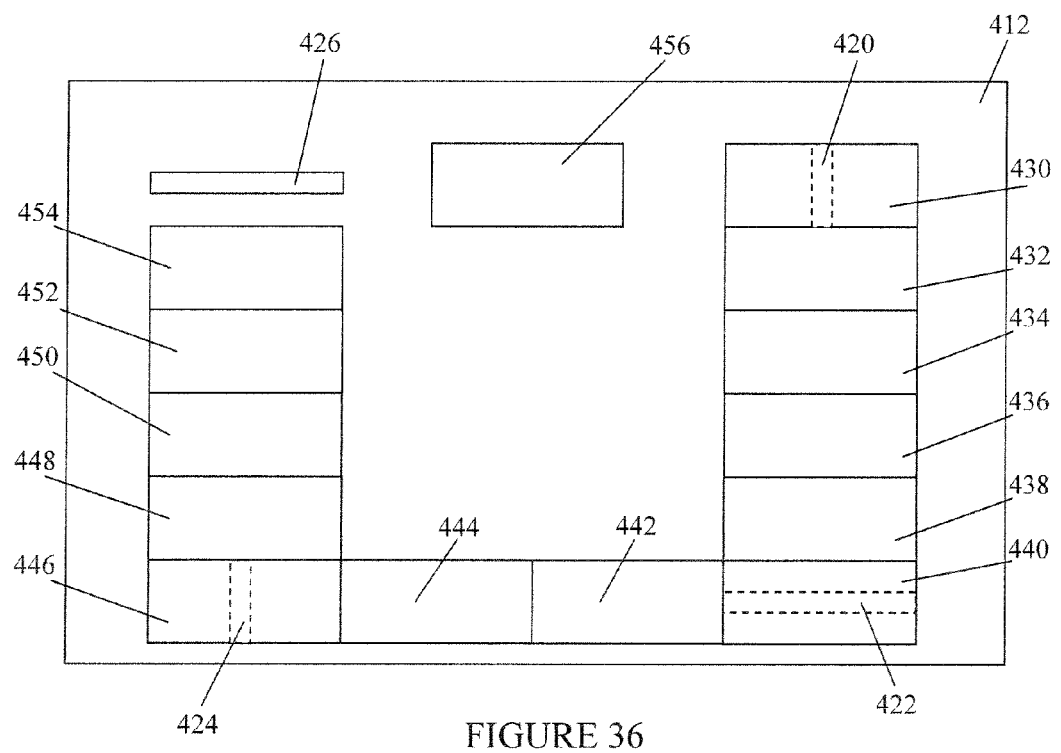
FIG. 36 is a block diagram illustrating a fifth disposition of sample holders on the conveyor of FIG. 31, in accordance with an embodiment.
Figure 37:
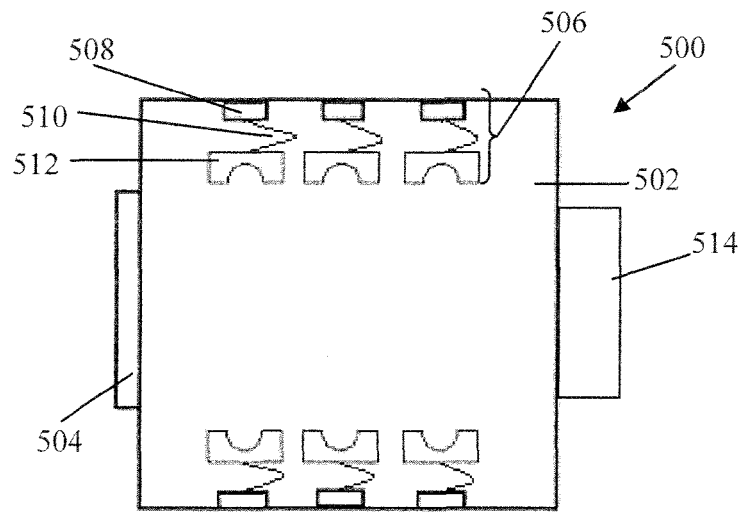
FIG. 37 is a block diagram of a heating chamber provided with microwave applicators comprising movable cavity portions in a retracted position, in accordance with an embodiment.

Referring back to FIG. 31, the sample holder 430 is located in the heating chamber 402 while the sample holders 432 and 434 are in the cooling station and the venting station, respectively. Once the heating of the sample holder 430 is completed, the conveyor belt 424 is activated to move the sample holders 448-456 towards the available position 458. The position on top of the conveyor belt 424 becomes the available position as illustrated in FIG. 33. The conveyor belt 422 is then activated to move the sample holders 442-446 towards the conveyor belt 424. Once the sample holder 446 has reached the position on top of the conveyor belt 424, the position on top of the conveyor belt 422 becomes the available position, as illustrated in FIG. 34. The conveyor belt 420 is then activated to move the sample holders 432-440 towards the conveyor belt 422. Once the sample holder 440 reaches the position on top of the conveyor belt 422, the position on top of the conveyor belt 420 is available and the sample holder 432 is in the venting station of the automated digestion system, as illustrated in FIG. 35. Then the sample holder 430 is moved from the heating chamber 402 to the cooling station 404 while the sample holder 456 enters the heating chamber 402. It should be understood that any mechanical positioning device may be used for moving a sample holder inside the heating chamber 402 and moving a sample holder from the heating chamber to the cooling station on top of the conveyor belt 420, and likewise from the cooling station to the venting station FIG. 37 illustrates one embodiment of a microwave oven 500 adapted to independently heat six samples. The oven 500 comprises a chamber 502 adapted to receive sample holders and provided with a microwave barrier door 504 for opening and closing the oven 500. The oven 500 also comprises six microwave applicators 506 each for individually applying microwaves to a different sample holder. Each microwave applicator 506 comprises a microwave generator 508 such as a magnetron for example, a flexible microwave waveguide 510 such as coaxial cable, and an oven cavity portion 512. The oven 500 further comprises a control unit 514 adapted to control the microwave applicators 506. In this embodiment, the oven cavity portion 512 is movable with respect to the microwave generator 508 between an extended position and a retracted position (illustrated in FIG. 37) and the length of the flexible microwave waveguide 510 is chosen to allow the displacement of the oven cavity portion 512 between the two positions.

Figure 38:
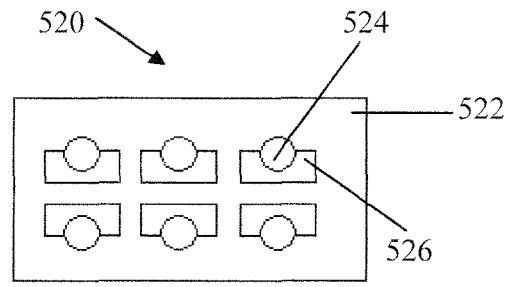
FIG. 38 is a block diagram illustrating a rack provided with cavity portions, in accordance with an embodiment.

FIG. 38 illustrates one embodiment of a sample holder 520 adapted to the oven 500. The sample holder 520 comprises a rack 522 adapted to receive six sample tubes 524. The sample holder 520 also comprises six rack cavity portions 526. Each rack cavity portion 526 is adapted to form a microwave cavity when physically connected to a respective oven cavity portion 512. The rack cavity portions 526 are positioned on the rack 522 in accordance with the position of the oven cavity portions 512 when in the extended position. It should be understood that the sample tubes 524 may be removably secured to the rack 522.

Figure 39:
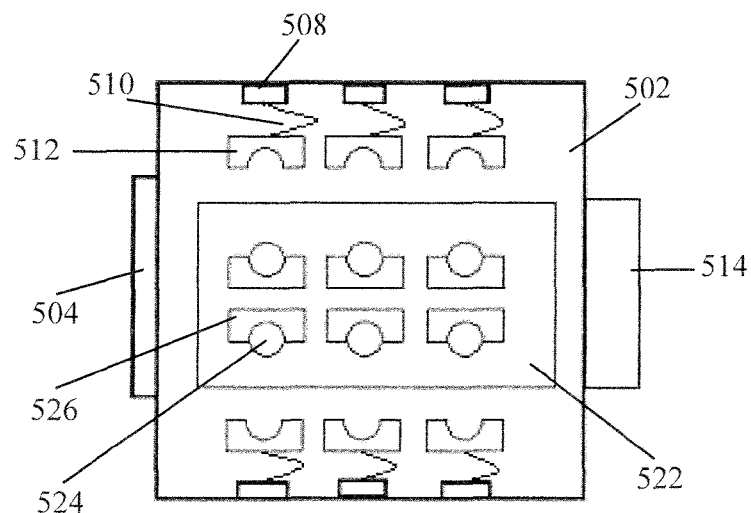
FIG. 39 is a block diagram illustrating the rack of FIG. 38 inserted into the heating chamber of FIG. 37 when the movable cavity portions are in the retracted position, in accordance with an embodiment.

FIG. 39 illustrates the sample holder 520 received in the microwave oven 500. The sample holder 520 is positioned within the oven 500 so that each rack cavity portion 526 faces a corresponding oven cavity portion 512.

In one embodiment, a mechanical positioning device is used to precisely position the sample holder 520 within the oven 500. Positioning sensors such as optical or mechanical sensors may be used to determine the position of the sample holder 520. It should be understood that the mechanical positioning device may be controlled by the control unit 514 of the oven 500.

In another embodiment, abutting elements are located in the oven 500 to precisely position the sample holder 520 with respect to the oven cavity portions 512.

In a further embodiment, the sample holder 520 is positioned in the oven 500 by a user.

Figure 40:
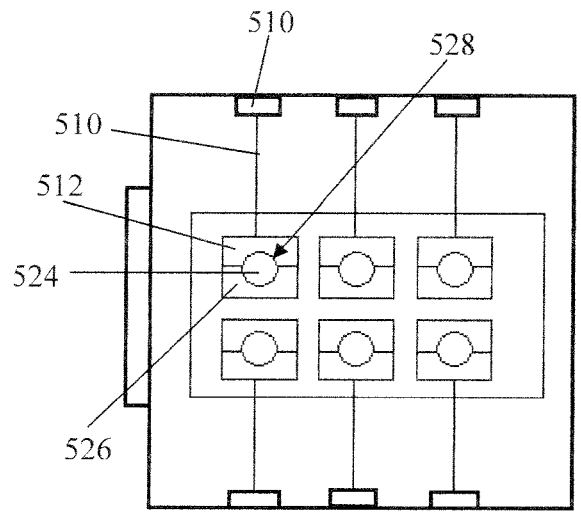
FIG. 40 is a block diagram illustrating the rack of FIG. 38 inserted into the heating chamber of FIG. 37 when the movable cavity portions are in the extended position, in accordance with an embodiment.

Once the sample holder 520 has been precisely positioned in the oven 500, the oven cavity portions 512 are moved from the retracted position (FIGS. 37 and 39) to the extended position, as illustrated in FIG. 40. In the extended position, each oven cavity portion 512 engages a corresponding rack cavity portion 526. As the oven cavity portion 512 and the rack cavity portion 526 are complementary portions of a mini microwave cavity 528, the mini microwave cavity 528 is formed when the oven cavity portion 512 engages the rack cavity portion 526. It should be understood that the oven cavity portion 512 and the rack cavity portion 526 are made from microwave reflecting material such as metal, for example aluminum, and designed so that the mini cavity 528 is substantially hermetical to microwaves, i.e. so that substantially no microwaves exit the cavity at the junction of the oven cavity portion 512 and the rack cavity portion 526.

While the present description refers to a rack 520 having six rack cavity portions 526 and an oven 500 having six oven cavity portions 512, it should be understood that the number of cavity portions is exemplary only as along as the rack 520 and the oven 500 each comprise at least two respective cavity portions.

Figure 41:
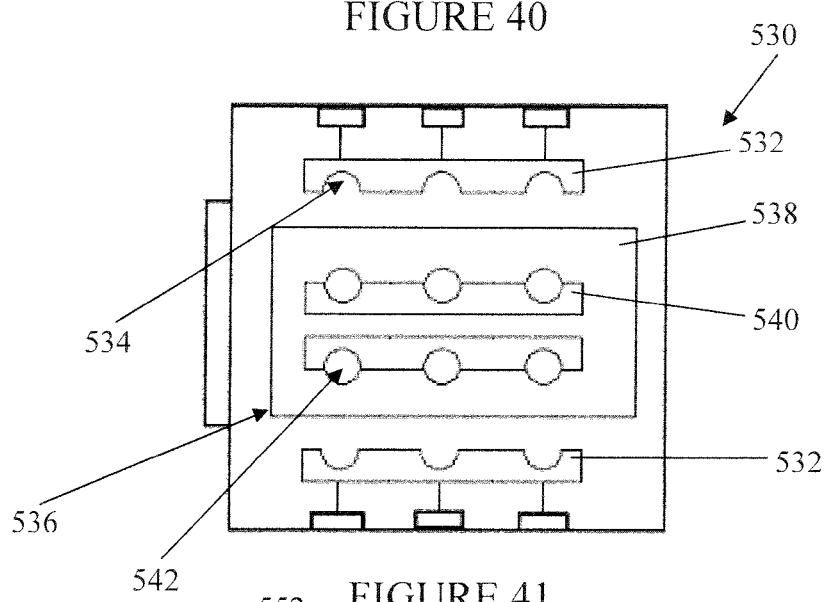
FIG. 41 is a block diagram illustrating a heating chamber provided with two cavity elements having cavity recesses, in accordance with an embodiment.

While FIGS. 37 to 40 illustrate an oven 500 comprising two rows of physically spaced oven cavity portions 512 and a rack 520 comprising two rows of physically spaced rack cavity portions 526, it should be understood that other embodiments are possible. For example, FIG. 41 illustrates one embodiment of a microwave oven 530 comprising two oven cavity elements 532 each having three recesses 534 each forming an oven cavity portion. The oven 530 is adapted to receive a sample holder 536 comprising a rack 538 on which two rack cavity elements 540 are secured. Each rack cavity element 540 comprises three recesses 542 each forming a rack cavity portion.

Figure 42:
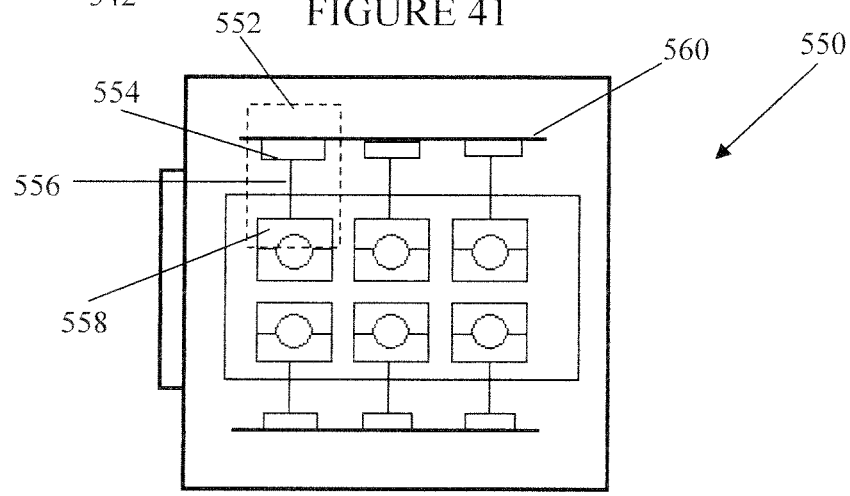
FIG. 42 is a block diagram illustrating a heating chamber having movable microwave applicators, in accordance with an embodiment.

While FIG. 37 illustrates an oven 500 comprising movable oven cavity portions 512, it should be understood that other embodiments are possible. For example, FIG. 42 illustrates one embodiment of a microwave oven 550 comprising six movable microwave applicators 552. Each microwave applicator 552 comprises a microwave generator 554 and an oven cavity portion 558 connected together by a microwave waveguide 556. The microwave waveguide 556 may be flexible. Alternatively, the microwave waveguide 556 may be rigid. The microwave applicators 552 are secured to two displacement plates 560 to form two rows of microwave applicators 552. By moving one displacement plate 560, three microwave applicators 552 are moved. Alternatively, each microwave applicator 552 may be independently movable.

While FIG. 40 illustrates a mini microwave cavity 528 designed to match the shape of the sample tube 524, it should be the mini cavity may have any adequate shape and size. FIG. 43 illustrates one embodiment of a square mini microwave cavity 570 formed when an oven cavity portion 572 engages a rack cavity portion 574. The internal perimeter of the square mini microwave cavity 570 is superior to the external perimeter of the cylindrical sample tube 524 so that the sample tube 524 does not engage the walls of the cavity 570.

FIG. 44 illustrates one embodiment of a mini microwave cavity 580 formed by engaging an oven cavity portion 582 with a rack cavity portion 584. The oven cavity portion comprises a U-Shaped microwave reflecting plate 586 having an internal groove and a protective element 588 positioned in the groove of the plate 586. An antenna 590 having a shape matching that of the groove is inserted between the plate 586 and the protective element 588. The antenna may be curved, vertical, or other. The antenna 590 is connected to a power generator via a microwave waveguide 592 and is used to emit microwaves in the cavity 580. The rack cavity portion 584 comprises a U-shaped microwave reflecting plate 594 having a groove in which a protective element 596 may be inserted.

The protective elements 588 and 596 are made from a material transparent to microwaves such as Teflon for example, while the U-shaped plates 586 and 594 are made from a material capable of reflecting microwaves such as metal (aluminum, etc).

It should be understood that the mini microwave cavity may have any adequate height with respect to that of the sample tube to be received therein. For example, the height of the oven and rack cavity portions may be substantially equal to that of the sample tube. Alternatively, the height of the oven and rack cavity portion may be less than that of the sample tube.

FIG. 45 illustrates one embodiment of an automated digestion system provided with a control unit (not shown) and a closed loop conveyor for directing a plurality of sample holders 604 in a heating chamber 605, a cooling station 606, and a venting station 608. Each sample holder 604 comprises at least one rack cavity portion 610 adapted to receive a hermetically closed or open sample tube 612. The heating chamber 605 is provided with at least one movable oven cavity portion 614 connected to a microwave generator and adapted to form a mini microwave cavity when connected to a corresponding rack cavity portion 610. In some embodiments, two or more rack cavity portions 610 are provided in the heating chamber 605.

When a sample holder 604 enters the heating chamber 605, a positioning device (not shown) precisely positions the sample holder 604 with respect to the position of the oven cavity portions 614. Then, the oven cavity portions 614 are moved to their extended position in order to engage their respective rack cavity portion 610, thereby forming a mini microwave cavity.

The sample contained in each sample tube 612 may be independently heated by applying sample specific parameters. The independent mini microwave cavities allow each individual sample to be heated to a sample specific temperature, for a sample specific amount of time. Therefore, each sample of a sample holder 604 containing a given number of samples may be different, and the sample specific parameters can be applied to each sample accordingly. Various heating programs may be created using a combination of heating and non-heating times and a plurality of heating temperatures. The sample holder 604 is maintained in the heating chamber 605 until the last sample has completed its heating program.

The sample-specific heating parameters may comprise a desired temperature, and/or a microwave power, and/or a duty cycle, and/or a heating time, and/or sample parameters such as an identification of the sample or the quantity of sample contained in the sample tube, and/or tube parameters such as the volume of the tube or the material of the tube, and/or the like. The automated digestion system 600 is adapted to identify a particular sample tube 612 and independently heat each sample tube 612 in accordance with the sample specific parameters. In one embodiment, the automated digestion system 600 is provided with a bar code reader and the sample parameters are retrieved by the control unit by reading the bar code of the sample container.

In one embodiment, the sample holder 604 is provided with an ID, such as a bar code or a RF ID for example, for each sample tube 612 and the automated digestion system 600 is provided with an ID reader adapted to read the sample tube ID. Alternatively, the sample ID may be located on the sample tube 612.

In another embodiment, the rack is provided with an internal clock and the automated digestion system 600 is provided with a reader capable of identifying the sample holders 604 using the internal clock. One series of magnets are used to activate a sensor (the reader), and another series of magnets are used as the clock. The clock corresponds to an ID for the sample holder 604.

Once the heating process is completed, the oven cavity portions are moved to their retracted position and the sample holder 604 is moved to the cooling station 606 to be cooled. Once cooled, the sample holder 604 is brought to the venting station 608 where an unsealing system unseals the sample tubes, thereby providing an auto-venting of the sample tubes. In one embodiment, moving the sample holder 604 from the cooling station 606 to the venting station 608 occurs when the samples in the sample tubes 612 at the cooling station 606 have reached a pre-determined temperature.

Figure 46:
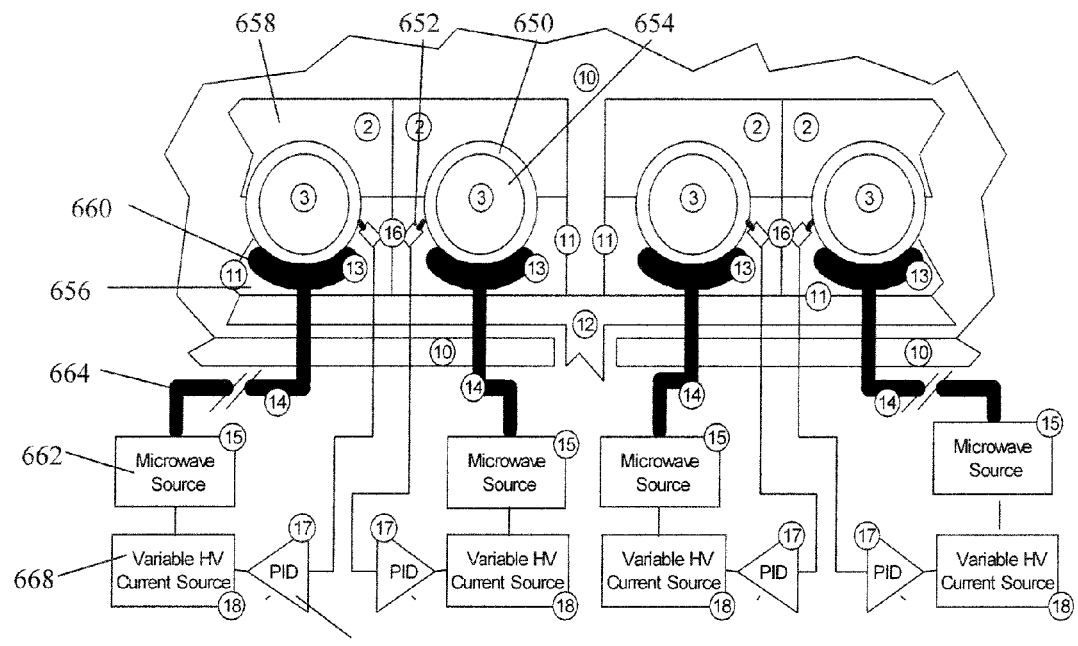
FIG. 46 is a top view of mini cavities provided with a temperature sensor, in accordance with an embodiment.

FIG. 46 illustrates one embodiment of mini microwave cavities 650 each comprising a temperature sensor 652 for sensing the temperature of a sample contained in a vessel or sample tube 654. In this embodiment, the temperature sensors sit below each vessel underneath a floor of the heating chamber. A series of apertures are provided in the floor of the heating chamber to allow the temperature sensors to access the vessels. Individual temperature control of each sample in each vessel is provided.

Each mini cavity 650 is formed by a movable oven cavity portion 656 and a rack cavity portion 658. An antenna 660 is connected to a microwave source 662 by a microwave waveguide 664. For each mini cavity 650, a proportional-integral-derivative (PID) controller 666 receives the sensed temperature from a temperature sensor 652. In order to reach a desired sample temperature, the PID controller 666 adjusts the amount of microwave energy delivered by the microwave source 662 to the antenna 660 by controlling an adjustable high voltage current source 668 powering the microwave source 662. Although FIG. 46 illustrates a configuration comprising one microwave source per mini cavity, another embodiment may comprise one microwave source and a splitter for multiple cavities.

Figure 47:
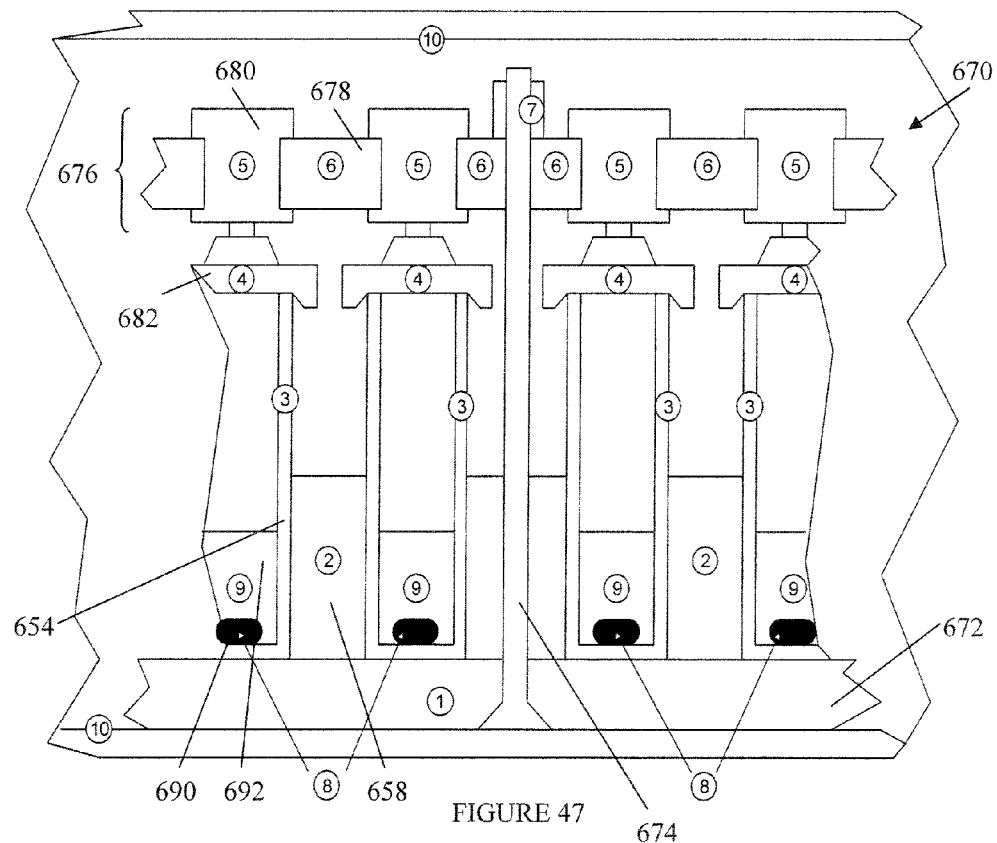
FIG. 47 is a side view of a rack provided with rack cavity portions and a rack cover having pressure-relief valve caps, in accordance with an embodiment.

FIG. 47 illustrates one embodiment of a sample holder 670 comprising the rack cavity portions 658. The sample holder 670 comprises a rack formed by a base plate 672 and a stud 674, and a rack cover 676. The rack cover comprises a cap-receiving plate 678 to which compression caps 680 are removably secured. The vessels 654 are received in the rack and sealed by a sealing cap 682. Then the rack cover 676 is secured on top of the rack so that a compression cap 680 abuts against a corresponding sealing cap 682 for hermetically closing the vessels 654.

In an alternative embodiment, open vessels are used that do not require the rack cover plate 676. In this case, cap 682 may or may not be set on top of the vessel 654.

While the sample holder 670 is provided with a rack cover 676 provided with a pressure-relief valve system, it should be understood that the vessels 654 may be closed by the sealing caps 682. Alternatively, the vessels 654 may be left open during the heating process.

In one embodiment, each vessel 654 contains a sample 690 and a liquid solution 692 and is positioned into its respective mini cavity 650 so that the sample 690 and the solution 692 present an RF load matching that of the antenna 660. This maximizes energy transfer to the solution 692 and minimizes energy reflection towards the microwave source 662.

Figure 48:
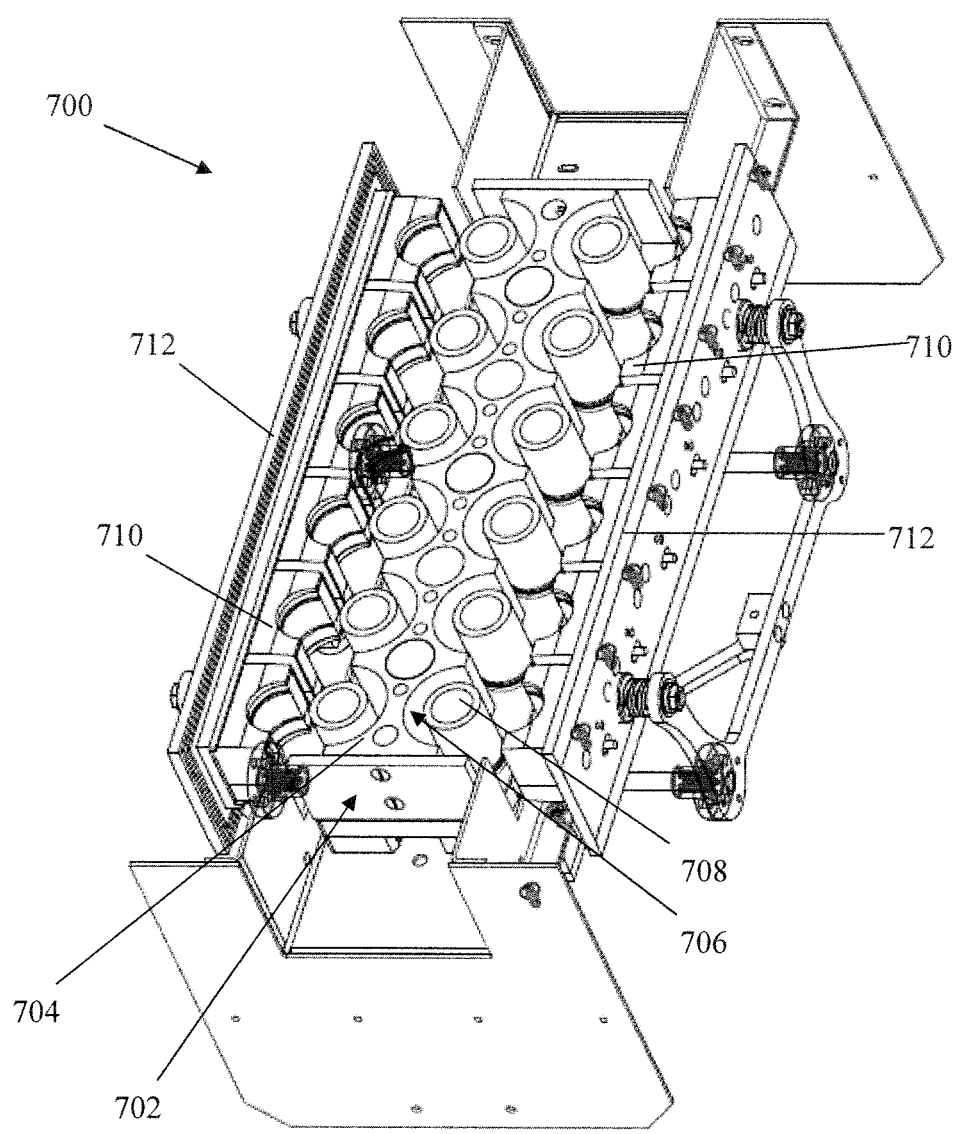
FIG. 48 is a perspective view of a closing mechanism for forming mini microwave cavities, in accordance with an embodiment.

FIG. 48 illustrates one embodiment of a mini cavity assembly 700 in which the rack cavity portions are made of a single piece. The rack 702 comprises a cavity element 704 in which grooves 706 are made on opposite sides thereof. Each groove 706 corresponds to a rack cavity portion and a sample tube 708 is inserted into the grooves. Oven cavity portions 710 are regrouped into two rows and each row of oven cavity portions 710 is secured to a translation plate 712. The translation plates 712 are activated by a motor (not shown) to engage the oven cavity portions 710 with the rack cavity element 704 to form the mini cavities.

Figure 49:
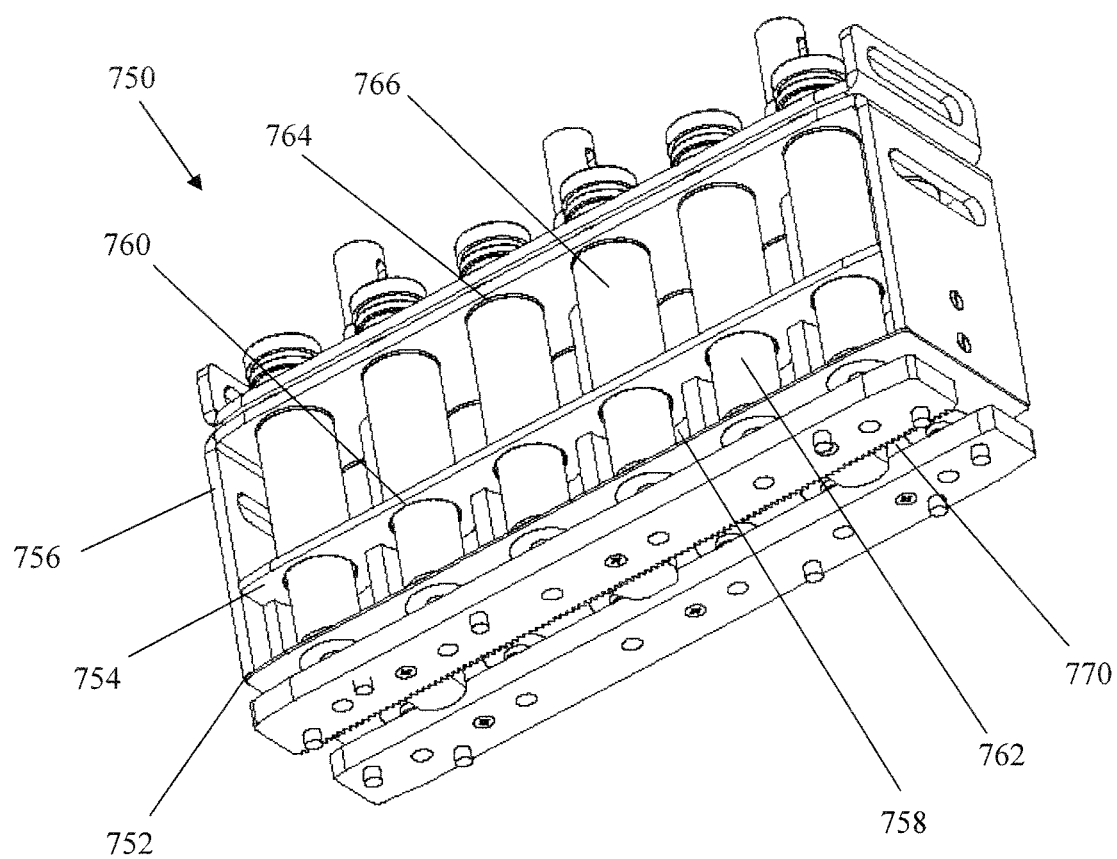
FIG. 49 is a perspective view of a rack provided with rack cavity portions, in accordance with an embodiment.

FIG. 49 illustrates one embodiment of a rack 750 provided with rack cavity portions and a microwave cross-talk preventing device. The rack 750 comprises a base plate 752 to which a cavity plate 754 and a U-shaped plate 756 are secured. Recesses 758 are made in the cavity plate 754 to form six rack cavity portions on each side of the cavity plate 754. Twelve openings 760 each aligned with a recess 758 and adapted to receive a sample tube 762 are made on top of the cavity plate 754. The U-shaped plate 756 is provided with twelve tube receiving openings 764 each aligned with a respective opening 760. The rack 750 further comprises twelve microwave reflecting cylinders 766 each secured on top of the cavity plate 754 and aligned with a respective opening 760 so that a sample tube 762 may be received in the openings 760 and 764 and the hollow cylinder 766. The reflecting cylinders 766 serve as a microwave cavity extender to prevent cross talk and extend the microwave energy to samples that exceed the size (volume) of the microwave cavity.

The rack 750 is inserted into a heating chamber provided with oven cavity portions matching the rack cavity portions to form twelve mini microwave cavities. The cylinders 766 acts as a microwave barrier reducing or substantially preventing the propagation of microwaves from one mini cavity to another. It should be understood that the cylinders 766 are made from a microwave reflecting material such as metal or aluminum for example.

In one embodiment, an automated digestion system such as the system 400 is provided with a heating chamber comprising at least oven cavity portions and adapted to receive a rack comprising rack cavity portions. For example, the rack 750 may be used for heating samples in such an automated digestion system.

In one embodiment, the base plate 752 of the rack 750 is provided with a toothed groove 770 adapted to engage a gear having mesh teeth. The gear may be located in the heating chamber for precisely positioning the rack 750 in the heating chamber so that each rack cavity portion faces its respective oven cavity portion. The gear may also be used to bring the rack in the heating chamber and/or the cooling chamber.

In one embodiment, the base plate 752 is provided with at least four balls or low friction feet rotatably secured thereto for allowing the rack 750 to roll or slide on a substantially planar surface. In one embodiment, the front portion of the rack 750 must firstly enter in the heating chamber. In this case, only one side of the groove 770 is provided with teeth. This allows the gear not to engage with the groove if the rear portion of the rack is firstly presented to the gear.

In one embodiment, the base plate 752 is provided with twelve base plate openings each located beneath a corresponding sample tube 762 and the heating chamber is provided with twelve temperature sensors such as IR sensors. When the rack 750 enters the heating chamber and the mini cavities are formed, each temperature sensor is positioned below a respective base plate opening for measuring the temperature of a respective sample contained in the corresponding sample tube 762.

Figure 50:
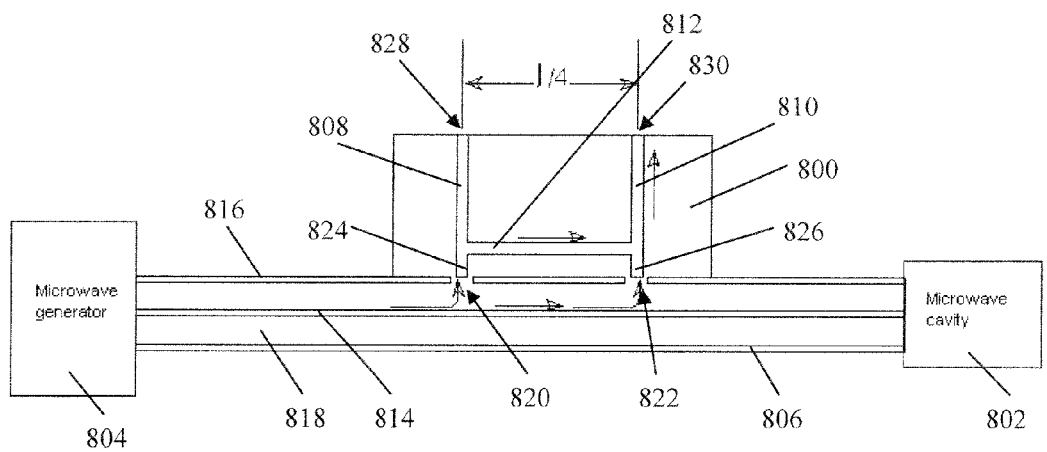
FIG. 50 is a block diagram of a directional coupler for measuring the power of a signal transmitted by a microwave generator to a microwave cavity, in accordance with an embodiment.

FIG. 50 illustrates one embodiment of a reflected power measuring device 800 for measuring the power reflected by a microwave cavity 802. The microwave cavity 802 is connected to a microwave generator 804 by a coaxial cable 806. The measuring device 800 comprises a directional coupler having a first RF waveguide 808 coupled to a second RF waveguide 810. The first and second RF waveguides 808 and 810 are spaced apart by a distance corresponding to a quarter of the wavelength of the RF signal propagating between the microwave generator 804 and the microwave cavity 802. The distance could also be ¾ of the wavelength, ⁵⁄₄ of the wavelength, etc. The coaxial cable 806 comprises a central core 814 and a shield 816 separated by a dielectric 818. Two holes 820 and 822 are made in the shield 816 of the coaxial cable 806. The two holes 820 and 822 are spaced apart by a distance corresponding to a quarter of the wavelength of the RF signal propagating between the microwave generator 804 and the microwave cavity 802. The first end 824 of the first waveguide 808 is inserted into the first hole 820 while the first end 826 of the second waveguide 810 is inserted into the second hole 822.

Figure 51:
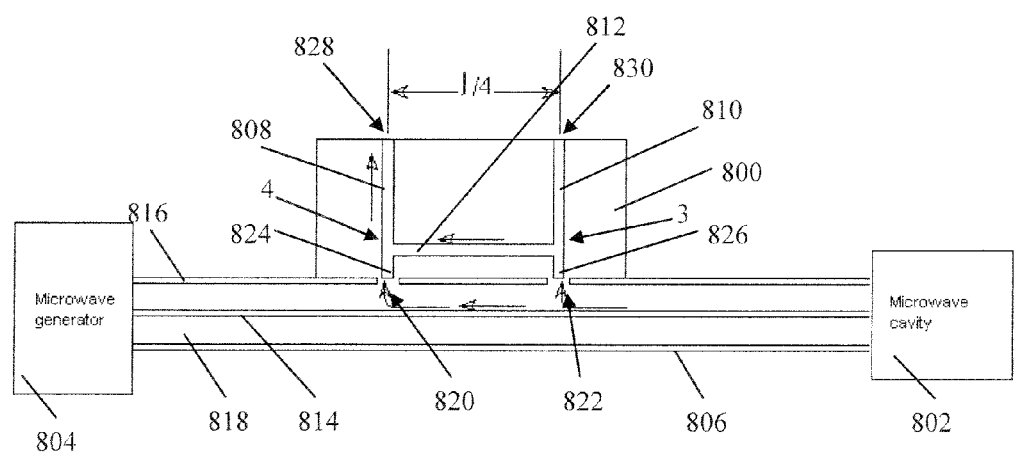
FIG. 51 is a block diagram of the directional coupler of FIG. 50 when used for measuring the power of a signal reflected by the microwave cavity, in accordance with an embodiment.

When an RF signal propagates from the microwave generator 804 to the microwave cavity 802, a part of the signal propagating in the core 814 of the coaxial cable 806 leaks via the first and second holes 820 and 822 and is coupled to the first end 824 of the first waveguide 808 and to the first end 826 of the second waveguide 810. Because the length of a third waveguide 812 is equal to the quarter of the wavelength of the RF signal, no signal propagates at the output 828 of the first waveguide. As illustrated in FIG. 51, at the tee junction in port 4, the signal coming from hole 820 is split in two parts, one going to port 3 and another going up to the output 828. At the tee junction in port 3, the signal coming from hole 822 is split in two parts, one going to port 4 and another going up to the output 830. The signal coupled at port 3 is going in the opposite direction and will be subtracted at port 4. Because the separation between the ports 3 and 4 is equal to a quarter wavelength, the signal coming from port 4 and going towards the output 828 is cancelled. As a result only one signal exits the directional coupler 800 by the output 830. The signal collected at the output 830 may be used for determining the power of the RF signal propagating from the microwave generator towards the microwave cavity 802.

FIG. 51 illustrates the propagation of an RF signal reflected by the cavity 802 and propagating from the cavity 802 towards the microwave generator 804. Following the same reasoning as for a signal propagating from the generator 804 towards the cavity 802, no signal is propagated towards the output 830 while the signal exiting the coupler 800 at the output 828 may be used for determining the power of the signal reflected by the cavity 802.

In one embodiment, the waveguides 808, 810, and 812 are microstrip lines. In another embodiment, the waveguides 808, 810, and 812 are striplines.

In one embodiment, because the coaxial cable 806 is part of the directional coupler, the cable 806 is not sliced in multiple sections to build a coupler and a high decoupling factor is obtained, thereby rendering the coupler 800 adequate for high power applications.

In one embodiment in which the RF signal propagation speed in the waveguides 808, 810, and 812 and in the coaxial line 806 are different, the coupler 800 comprises a dielectric substrate on which the waveguides 808, 810, and 812 are deposited and the dielectric constant of the substrate is chosen to render the RF signal propagation speed in the waveguides 808, 810, and 812 substantially equal to that in the coaxial cable 806. In the case where the propagation speed of a signal in a coaxial line is larger than in microstrip or stripline, the separation of holes 820 and 822 is equal to ¼ of wavelength in the coaxial cable and the length of line 812 is equal to ¾ wavelength. In this case, the coupled signal when the propagation is coming from generator 804 to cavity 802 will be at 828 and canceled at 830, and vice versa for reflecting signals.

In one embodiment, the hole is sized so that the coupling factor between the coaxial cable 806 and the coupler 800 is about −55 dB or less. This configuration is suitable for high power applications. In other embodiments, the coupling factor could be other than −55 dB for low power applications.

Figure 52:
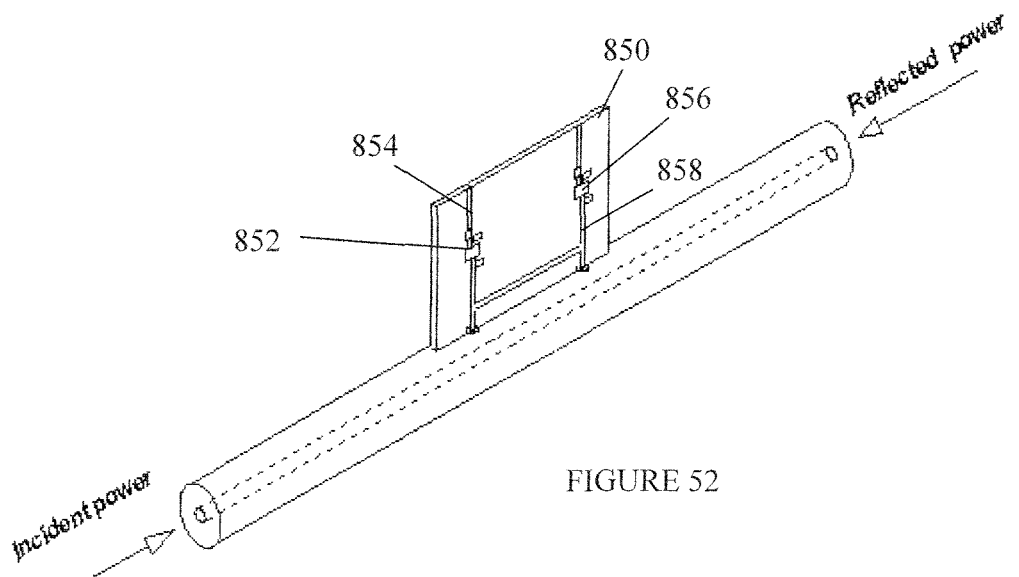
FIG. 52 is a perspective view of the directional coupler comprising detecting diodes and connected to a coaxial cable, in accordance with an embodiment.

FIG. 52 illustrates one embodiment of a coupler 850 comprising a detecting diode 852 used for measuring the power of a signal propagating in the first waveguide 854 and therefore determining the microwave power reflected by the cavity. The coupler 850 further comprises a second detecting diode 856 used for measuring the power of a signal propagating in the second waveguide 858 and therefore determining the microwave power generated by the microwave generator.

In one embodiment, the isolation between the ports is substantially equal to −10 dB.

In one embodiment, a matching on output ports is achieved in order to maintain a good isolation between the cavity 802 and port 3, and the microwave generator 804 and port 4.

Figure 53:
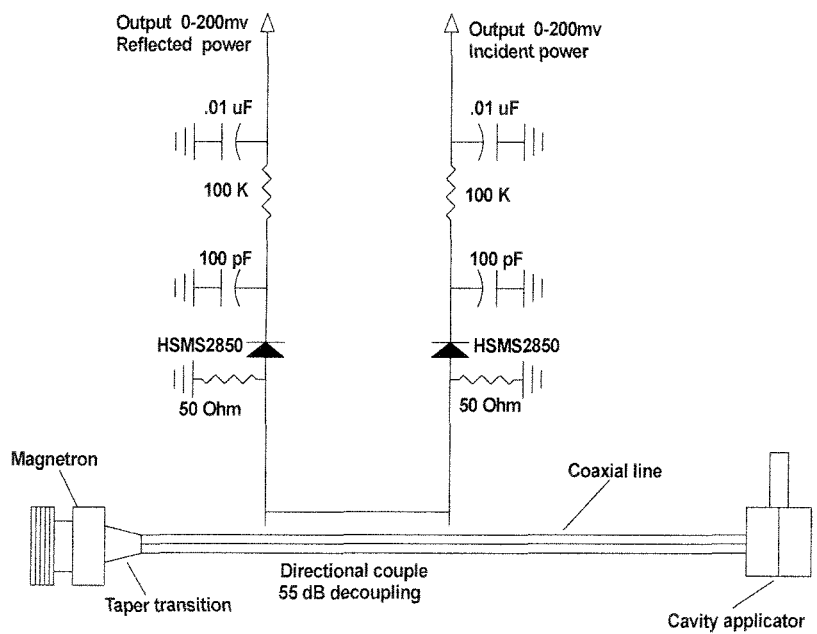
FIG. 53 is a schematic representation of a directional coupler comprising Schottky zero bias diodes, in accordance with an embodiment.

FIG. 53 illustrates one embodiment of a coupler provided with a detector for measuring the reflected power and another detector for measuring the incident power. Each detector comprises a Schottky zero bias diode that transforms the microwave signal into a DC voltage. In one embodiment, the detector is linear in the square law range means below −5 dBm. In one embodiment in which the coupling factor is about −55 dB, the detector is substantially linear for input powers as large as 50 dBm means 100 Watts, and can detect powers up to 60 dBm means 1000 Watts. In one embodiment, an input resistor is used to match the circuit and the result is about −15 dB which is lower than the directivity of coupler.

In one embodiment, the detected reflected power is used for determining cavity problems such as a missing sample tube, the complete evaporation of the sample contained into the cavity, the absence of a sample into a sample tube, the explosion of a sample tube, and the like. Upon detection of a problem, the generation of microwaves may be stopped and an alarm may be triggered.

In one embodiment, the detected incident power may be used for detecting microwave source problems.

While the present description refers to digestion of samples, it should be understood that the methods, apparatuses, devices, and system described above may be used for extraction.

It should be noted that the embodiments described above are intended to be exemplary only. Solely the scope of the appended claims is limitative.

We claim:

1. An automated heating system for heating a plurality of samples contained in a sample holder, comprising:
    a heating chamber having at least one opening and adapted to receive the sample holder;
    at least one microwave generator in microwave transfer communication with the heating chamber for propagating thereinto microwaves to perform digestion of the plurality of samples by at least one chemical decomposition agent;
    a conveyor adapted to receive and transport the sample holder into and out of the heating chamber;
    at least one microwave barrier movable between an open position to allow access to the heating chamber and a closed position to prevent the microwaves from leaking out of the heating chamber when the at least one microwave generator is activated; and
    a control unit configured to control a temperature of each one of the plurality of samples contained in the sample holder independently from remaining ones of the plurality of samples by controlling the conveyor and the at least one microwave generator in an automated manner.

2. The automated heating system of claim 1, further comprising a cooling station downstream from the heating chamber, the cooling station operatively connected to the heating chamber via the conveyor.

3. The automated heating system of claim 2, wherein the cooling station comprises an enclosed cooling chamber and a cooling unit for cooling the sample.

4. The automated heating system of claim 3, wherein the cooling unit comprises at least one fan or compressed gases in fluid communication with the cooling chamber.

5. The automated heating system of claim 3, wherein the cooling unit is controlled by the control unit.

6. The automated heating system of any one of claims 2 to 5, further comprising a venting station downstream from the cooling station, the venting station operatively connected to the cooling station via the conveyor.

7. The automated heating system of claim 6, wherein the venting station comprises a venting chamber and an unsealing unit for unsealing the sample holder to allow venting of the sample.

8. The automated heating system of claim 7, wherein the unsealing unit comprises an automated mechanism for unlocking a sealing cap sealing the sample in the sample holder.

9. The automated heating system of claim 7, wherein the venting station comprises a positioning device to align the sample holder with the unsealing unit.

10. The automated heating system of claim 7, wherein the unsealing unit is controlled by the control unit.

11. The automated heating system of claim 6, wherein the heating chamber, the cooling station, and the venting station form a closed loop with the conveyor.

12. The automated heating system of claim 11, wherein the system is enclosed in a portable casing.

13. The automated heating system of claim 1, wherein the at least one opening comprises an entrance opening and an oppositely facing exit opening, the at least one microwave barrier comprises a first barrier for said entrance opening and a second barrier for said exit opening, and the conveyor extends through the heating chamber via the entrance opening and the exit opening.

14. The automated heating system of claim 13, wherein the control unit is adapted to control the opening and closing of the first barrier and the second barrier.

15. The automated heating system of claim 1, wherein the control unit comprises a memory, a processor, and an input device, and is adapted to adjust at least one of a power level of the at least one microwave generator, a duty cycle of the at least one microwave generator, and a duration of time for applying microwaves, in accordance with an input setting.

16. The automated heating system of claim 15, wherein the control unit is adapted to control a speed of displacement and a position of the sample holder via the conveyor.

17. The automated heating system of claim 1, further comprising an identification reader for identifying a given sample in the sample holder, and the control unit is adapted to receive the identification and apply a set of parameters corresponding to the given sample for controlling the temperature of the given sample independently.

18. The automated heating system of claim 17, wherein the identification reader is in the conveyor and is adapted to read the identification from an underside of the sample holder.

19. The automated heating system of claim 1, further comprising at least one temperature sensor operatively connected to the control unit.

20. The automated heating system of claim 1, further comprising position sensors operatively connected to the control unit.

21. The automated heating system of claim 1, wherein the heating chamber comprises at least one movable oven cavity portion connected to the at least one microwave generator and adapted to form a mini microwave cavity when connected to a corresponding one of at least one rack cavity portion provided with the sample holder, each of the at least one rack cavity portion adapted to receive a given one of the plurality of samples, for causing the microwaves to be independently applied to the given sample, thereby independently heating the given sample.

22. The automated heating system of claim 1, wherein the control unit is a closed-loop proportional-integral-derivative controller.

* * * * *